United States Patent
Langlois et al.

(10) Patent No.: US 9,925,071 B2
(45) Date of Patent: Mar. 27, 2018

(54) PROSTHETIC AND ORTHOTIC DEVICES AND METHODS AND SYSTEMS FOR CONTROLLING THE SAME

(71) Applicant: Össur hf, Reykjavik (IS)

(72) Inventors: David Langlois, St-Jacques-de-Leeds (CA); Matheson Rittenhouse, Montreal (CA); Yves Roy, Quebec (CA)

(73) Assignee: Össur hf, Reykjavik (IS)

( * ) Notice: Subject to any disclaimer, the term of this patent is extended or adjusted under 35 U.S.C. 154(b) by 0 days.

(21) Appl. No.: 14/549,278

(22) Filed: Nov. 20, 2014

(65) Prior Publication Data
US 2015/0081037 A1 Mar. 19, 2015

Related U.S. Application Data

(62) Division of application No. 13/248,532, filed on Sep. 29, 2011, now Pat. No. 8,915,968.
(Continued)

(51) Int. Cl.
*A61F 2/68* (2006.01)
*A61F 2/60* (2006.01)
(Continued)

(52) U.S. Cl.
CPC ............... *A61F 2/68* (2013.01); *A61F 2/60* (2013.01); *A61B 5/1123* (2013.01);
(Continued)

(58) Field of Classification Search
CPC ....................................................... A61F 2/70
See application file for complete search history.

(56) References Cited

U.S. PATENT DOCUMENTS

| 3,417,409 A | 12/1968 | Prahl |
| 3,701,368 A | 10/1972 | Stern |

(Continued)

FOREIGN PATENT DOCUMENTS

| CA | 1215614 | 12/1986 |
| CA | 2405356 | 10/2001 |

(Continued)

OTHER PUBLICATIONS

Abbas et al., "Neural Network Control of Functional Neuromuscular Stimulation Systems: Computer Stimulation Studies," IEEE Transactions on Biomedical Engineering, vol. 42, No. 11, Nov. 1995, pp. 1117-1127.

(Continued)

*Primary Examiner* — Jacqueline Woznicki
(74) *Attorney, Agent, or Firm* — Knobbe Martens Olson & Bear LLP

(57) ABSTRACT

Prosthetic and/or orthotic devices (PODS), control systems for PODS and methods for controlling PODS are provided. As part of the control system, an inference layer collects data regarding a vertical and horizontal displacement of the POD, as well as an angle of the POD with respect to gravity during a gait cycle of a user of the POD. A processor analyzes the data collected to determine a locomotion activity of the user and selects one or more control parameters based on the locomotion activity. The inference layer may be situated between a reactive layer control module and a learning layer control module of the control system architecture.

20 Claims, 6 Drawing Sheets

Related U.S. Application Data

(60) Provisional application No. 61/387,888, filed on Sep. 29, 2010.

(51) Int. Cl.
  *A61F 2/70* (2006.01)
  *A61F 2/76* (2006.01)
  *A61B 5/11* (2006.01)
  *A61F 2/64* (2006.01)

(52) U.S. Cl.
  CPC ......... *A61B 2560/0462* (2013.01); *A61F 2/64* (2013.01); *A61F 2/70* (2013.01); *A61F 2002/607* (2013.01); *A61F 2002/6827* (2013.01); *A61F 2002/701* (2013.01); *A61F 2002/702* (2013.01); *A61F 2002/704* (2013.01); *A61F 2002/705* (2013.01); *A61F 2002/708* (2013.01); *A61F 2002/762* (2013.01); *A61F 2002/763* (2013.01); *A61F 2002/764* (2013.01); *A61F 2002/765* (2013.01); *A61F 2002/7615* (2013.01); *A61F 2002/7625* (2013.01); *A61F 2002/7635* (2013.01); *A61F 2002/7645* (2013.01)

(56) References Cited

U.S. PATENT DOCUMENTS

| | | |
|---|---|---|
| 4,030,141 A | 6/1977 | Graupe |
| 4,179,759 A | 12/1979 | Smith |
| 4,521,924 A | 6/1985 | Jacobsen et al. |
| 4,556,956 A | 12/1985 | Dickenson et al. |
| 4,558,704 A | 12/1985 | Petrofsky |
| 4,600,357 A | 7/1986 | Coules |
| 4,805,455 A | 2/1989 | DelGiorno et al. |
| 4,843,921 A | 7/1989 | Kremer |
| 4,994,086 A | 2/1991 | Edwards |
| 5,062,857 A | 11/1991 | Berringer |
| 5,252,102 A | 10/1993 | Singer et al. |
| 5,282,460 A | 5/1994 | Boldt |
| 5,314,498 A | 5/1994 | Gramnaes |
| 5,383,939 A | 1/1995 | James |
| 5,443,524 A | 8/1995 | Sawamura et al. |
| 5,443,528 A | 8/1995 | Allen |
| 5,571,205 A | 11/1996 | James |
| 5,571,210 A | 11/1996 | Lindh |
| 5,571,213 A | 11/1996 | Allen |
| 5,650,704 A | 7/1997 | Pratt et al. |
| 5,704,946 A | 1/1998 | Greene |
| 5,746,774 A | 5/1998 | Kramer |
| 5,779,735 A | 7/1998 | Molino |
| 5,888,212 A | 3/1999 | Petrofsky et al. |
| 5,888,213 A | 3/1999 | Sears et al. |
| 5,888,236 A | 3/1999 | Van de Veen |
| 5,888,246 A | 3/1999 | Gow |
| 5,893,891 A | 4/1999 | Zahedi |
| 5,895,430 A | 4/1999 | O'Connor |
| 6,007,582 A | 12/1999 | May |
| 6,113,642 A | 9/2000 | Petrofsky et al. |
| 6,168,634 B1 | 1/2001 | Schmitz |
| 6,361,570 B1 | 3/2002 | Gow |
| 6,395,193 B1 | 5/2002 | Kintz et al. |
| 6,425,925 B1 | 7/2002 | Grundei |
| 6,443,995 B1 | 9/2002 | Townsend et al. |
| 6,494,039 B2 | 12/2002 | Pratt et al. |
| 6,610,101 B2 | 8/2003 | Herr et al. |
| 6,679,920 B2 | 1/2004 | Biedermann et al. |
| 6,695,885 B2 | 2/2004 | Schulman et al. |
| 6,755,870 B1 | 6/2004 | Biedermann et al. |
| 6,764,520 B2 | 7/2004 | Deffenbaugh et al. |
| 6,805,677 B2 | 10/2004 | Simmons |
| D499,487 S | 12/2004 | Bédard et al. |
| D501,925 S | 2/2005 | Bédard et al. |
| 6,875,241 B2 | 4/2005 | Christensen |
| 6,955,692 B2 | 10/2005 | Grundei |
| 6,966,882 B2 | 11/2005 | Horst |
| 7,137,998 B2 | 11/2006 | Bédard et al. |
| 7,147,667 B2 | 12/2006 | Bédard et al. |
| 7,313,463 B2 | 12/2007 | Herr et al. |
| 7,531,006 B2 | 5/2009 | Clausen et al. |
| 7,575,602 B2 | 8/2009 | Amirouche et al. |
| 7,637,957 B2 | 12/2009 | Ragnarsdottir et al. |
| 7,637,959 B2 | 12/2009 | Clausen et al. |
| 7,736,394 B2 | 6/2010 | Bédard et al. |
| 7,815,689 B2 | 10/2010 | Bédard et al. |
| 7,867,284 B2 | 1/2011 | Bédard et al. |
| 7,867,285 B2 | 1/2011 | Clausen et al. |
| 7,918,808 B2 | 4/2011 | Simmons |
| 7,955,398 B2 | 6/2011 | Bédard et al. |
| 8,007,544 B2 | 8/2011 | Jonsson et al. |
| 8,048,172 B2 | 11/2011 | Jonsson et al. |
| 8,057,550 B2 | 11/2011 | Clausen |
| 8,083,807 B2 | 12/2011 | Auberger et al. |
| 8,087,498 B2 | 1/2012 | Dupuis et al. |
| 8,211,042 B2 | 7/2012 | Gilbert et al. |
| 8,231,687 B2 | 7/2012 | Bédard et al. |
| 7,431,737 C1 | 12/2013 | Ragnarsdottir et al. |
| 7,896,927 C1 | 5/2014 | Clausen et al. |
| 8,915,968 B2 | 12/2014 | Langlois et al. |
| 2001/0029400 A1 | 10/2001 | Deffenbaugh et al. |
| 2004/0064195 A1 | 4/2004 | Herr |
| 2005/0137717 A1 | 6/2005 | Gramnaes |
| 2005/0216097 A1 | 9/2005 | Rifkin |
| 2006/0122710 A1* | 6/2006 | Bedard ............... A61F 2/644 623/24 |
| 2006/0135883 A1 | 6/2006 | Jónsson et al. |
| 2006/0184252 A1 | 8/2006 | Oddsson et al. |
| 2006/0184280 A1 | 8/2006 | Oddsson et al. |
| 2006/0224247 A1 | 10/2006 | Clausen et al. |
| 2006/0249315 A1 | 11/2006 | Herr et al. |
| 2007/0027557 A1 | 2/2007 | Jonsson et al. |
| 2007/0032748 A1 | 2/2007 | McNeil et al. |
| 2007/0043449 A1 | 2/2007 | Herr et al. |
| 2007/0050044 A1 | 3/2007 | Haynes et al. |
| 2007/0123997 A1 | 5/2007 | Herr et al. |
| 2007/0162152 A1 | 7/2007 | Herr et al. |
| 2007/0233279 A1 | 10/2007 | Kazerooni et al. |
| 2008/0046096 A1 | 2/2008 | Bédard et al. |
| 2008/0133171 A1 | 6/2008 | Feichtinger et al. |
| 2008/0300692 A1* | 12/2008 | Moser ............... A61F 2/6607 623/55 |
| 2009/0030344 A1 | 1/2009 | Moser et al. |
| 2009/0265018 A1 | 10/2009 | Goldfarb et al. |
| 2009/0299480 A1 | 12/2009 | Gilbert et al. |
| 2010/0042256 A1 | 2/2010 | Takenaka et al. |
| 2010/0131101 A1 | 5/2010 | Engeberg et al. |
| 2010/0179668 A1 | 7/2010 | Herr et al. |
| 2010/0262260 A1 | 10/2010 | Bédard et al. |
| 2010/0305716 A1 | 12/2010 | Pusch et al. |
| 2011/0125290 A1* | 5/2011 | Langlois ............... A61F 2/60 623/27 |
| 2011/0137429 A1* | 6/2011 | Bedard ............... A61F 2/644 623/24 |
| 2013/0095861 A1 | 4/2013 | Li et al. |
| 2013/0311133 A1 | 11/2013 | Kordari et al. |
| 2013/0311134 A1 | 11/2013 | Kordari et al. |
| 2014/0200680 A1 | 7/2014 | Holgate et al. |
| 2015/0018972 A1 | 1/2015 | Albrecht-Laatsch |

FOREIGN PATENT DOCUMENTS

| | | |
|---|---|---|
| CA | 2494365 | 3/2004 |
| CA | 2543061 | 6/2005 |
| CN | 2043873 | 9/1989 |
| CN | 2043873 U | 9/1989 |
| DE | 35 43 291 | 6/1987 |
| DE | 43 05 213 | 8/1993 |
| DE | 43 18 901 | 1/1994 |
| DE | 42 29 330 | 3/1994 |
| DE | 198 59 931 | 7/2007 |
| EP | 0 503 775 | 9/1992 |
| EP | 0 549 855 | 7/1993 |
| EP | 1 125 825 | 1/2001 |

(56) References Cited

FOREIGN PATENT DOCUMENTS

| | | |
|---|---|---|
| EP | 1 166 726 | 1/2002 |
| FR | 2 293 185 | 7/1976 |
| FR | 2 623 086 | 5/1989 |
| GB | 2 201 260 | 8/1988 |
| GB | 2 260 495 | 4/1993 |
| GB | 2 268 070 | 1/1994 |
| GB | 2 302 949 | 2/1997 |
| GB | 2 343 848 | 5/2000 |
| JP | 59-032453 | 2/1984 |
| JP | 59-071747 | 4/1984 |
| JP | 60-081530 | 5/1985 |
| JP | 11-056885 | 3/1999 |
| JP | 2001-277175 | 10/2001 |
| JP | 2002-191654 | 7/2002 |
| JP | 2002-533161 | 10/2002 |
| JP | 2003-250824 | 9/2003 |
| JP | 2005-500 | 1/2005 |
| KR | 10-2006-105026 | 10/2006 |
| WO | WO 96/041599 | 12/1996 |
| WO | WO 99/008621 | 2/1999 |
| WO | WO 00/038599 | 7/2000 |
| WO | WO 00/071061 | 11/2000 |
| WO | WO 01/054630 | 8/2001 |
| WO | WO 01/072245 | 10/2001 |
| WO | WO 02/080825 | 10/2002 |
| WO | WO 2005/051248 | 6/2005 |
| WO | WO 2006/024876 | 3/2006 |
| WO | WO 2008086629 A1 * | 7/2008 ............... A61F 2/60 |
| WO | WO 2011/057792 | 5/2011 |
| WO | WO 2011/100117 | 8/2011 |
| WO | WO 2011/100118 | 8/2011 |

OTHER PUBLICATIONS

Aminian et al., "Estimation of Speed and Incline of Walking Using Neural Network," IEEE Transactions on Instrumentation and Measurement, vol. 44, No. 3, Jun. 1995, pp. 743-746.

Andrews et al., "Hybrid FES Orthosis Incorporating Closed Loop Control and Sensory Feedback," Journal of Biomedical Engineering, vol. 10, Apr. 1988, pp. 189-195.

Au et al., Powered Ankle-Foot Prosthesis for the Improvement of Amputee Ambulation, Proceedings of the 29th Annual International Conference of the IEEE, Aug. 23-26, 2007.

Bachmann et al., Inertial and Magnetic Tracking of Limb Segment Orientation for Inserting Humans into Synthetic Environments, Naval Postgraduate School: Dissertation, Dec. 2000, pp. 199.

Bar et al., "Adaptive Microcomputer Control of an Artificial Knee in Level Walking," Journal of Biomechanical Engineering, vol. 5, Apr. 1983, pp. 145-150.

Baten et al., "Inertial Sensing in Ambulatory Back Load Estimation," 18th Annual International Conference of the IEEE Engineering in Medicine and Biology Society, Amsterdam, Oct. 31, 1996-Nov. 3, 1996, pp. 497-498.

Benedetti, "Gait Analysis of Patients Affected by Post-Traumatic Ankle Arthrosis Treated with Osteochondral Allograft Transplantation," SIAMOC 2006 Congress Abstracts/Gait & Posture 24S, 2006, p. S17.

Blaya, "Force-Controllable Ankle Foot Orthosis (AFO) to Assist Drop Foot Gait," Massachusetts Institute of Technology, Thesis, Feb. 2003 (believed to be catalogued on or after Jul. 8, 2003) in 97 pages.

Blumentritt et al., "Design Principles, Biomedical Data and Clinical Experience with a Polycentric Knee Offering Controlled Stance Phase Knee Flexion: A Preliminary Report", Journal of Prosthetics and Orthotics, vol. 9, No. 1, Winter 1997, pp. 18-24.

Bortz, "A New Mathematical Formulation for Strapdown Inertial Navigation," IEEE Transactions of Aerospace and Electronic Systems, vol. AES-7, No. 1, Jan. 1971.

Bouten et al., "A Triaxial Accelerometer and Portable Data Processing Unit for the Assessment of Daily Physical Activity," IEEE Transactions on Biomedical Engineering, vol. 44, No. 3, Mar. 1997, pp. 136-147.

Bouten et al., "Assessment of Energy Expenditure for Physical Activity Using a Triaxial Accelerometer," Medicine and Science in Sports and Exercise, vol. 26, No. 12, Aug. 1994, pp. 1516-1523.

Crago et al., "New Control Strategies for Neuroprosthetic Systems," Journal of Rehabilitation Research and Development, vol. 33, No. 2, Apr. 1996, pp. 158-172.

Dai et al., "Application of Tilt Sensors in Functional Electrical Stimulation," IEEE Transactions on Rehabilitation Engineering, vol. 4, No. 2, Jun. 1996, pp. 63-72.

Dietl et al., "Der Einsatz von Elektronik bei Prothesen zur Versorgung der unteren Extremität," Med. Orth. Tech., vol. 117, 1997, pp. 31-35.

Elliott, Scott B.; "MR Microprocessor-Controlled Swing and Stance," Presentation to American Academy of Orthotists & Prosthetists (Feb. 4, 2004), 81 pages.

Ferrari, First in vivo Assessment of "Outwalk", A Novel Protocol for Clinical Gait Analysis Based on Inertial and Magnetic Sensors.

Fisekovic et al., "New Controller for Functional Electrical Stimulation Systems," Medical Engineering & Physics, vol. 23, 2001, pp. 391-399.

Flowers et al., "An Electrohydraulic Knee-Torque Controller for a Prosthesis Simulator," Journal of Biomechanical Engineering: Transactions of the ASME; vol. 99, Series K, No. 1; Feb. 1977, pp. 3-8.

Foerster et al., "Detection of Posture and Motion by Accelerometry: A Validation Study in Ambulatory Monitoring," Computers in Human Behavior, vol. 15, 1999, pp. 571-583.

Foxlin et al., "Miniature 6-DOF Inertial System for Tracking HMDs," SPIE, vol. 3362, Apr. 13-14, 1998, pp. 15.

Frank et al., "Reliable Real-Time Recognition of Motion Related Human Activities Using MEMs Inertial Sensors," 2010, http://www.xsens.com/images/stories/PDF/Activity_Recognition_Final_ION_2010_Paper.pdf.

Fujita et al., "Joint Angle Control with Command Filter for Human Ankle Movement Using Functional Electrical Stimulation," Proceedings of the 9th Annual Conference of the IEEE Engineering in Medicine and Biology Society, Nov. 13-16, 1987, Ch. 2513, vol. 3, pp. 1719-1720.

Gard, Ph.D., Use of Quantitative Gait Analysis for the Evaluation of Prosthetic Walking Performance, Journal of Prosthetics & Orthotics, vol. 18, Issue 6, pp. P93-P104, Jan. 2006.

Godha et al., Integrated GPS/INS System for Pedestrian Navigation in a Signal Degraded Environment. ION GNSS 2006, Fort Worth TX, Sep. 26-29, 2006, p. 1-14.

Graps, Amara; "An Introduction to Wavelets," IEEE Computational Science & Engineering, vol. 2, No. 2, Summer 1995, pp. 50-61.

Hayes et al., "Leg Motion Analysis During Gait by Multiaxial Accelerometry: Theoretical Foundations and Preliminary Validations," Journal of Biomechanical Engineering, vol. 105, Aug. 1983, pp. 283-289.

Herr et al., "User-Adaptive Control of a Magnetorheological Prosthetic Knee," Industrial Robot: An International Journal, vol. 30, No. 1, 2003. pp. 42-55.

Heyn et al., "The Kinematics of the Swing Phase Obtained From Accelerometer and Gyroscope Measurements," 18th Annual International Conference of the IEEE Engineering in Medicine and Biology Society, Amsterdam 1996, pp. 463-464.

Howard, Russell Duane; "Joint and Actuator Design for Enhanced Stability in Robotic Force Control," Massachusetts Institute of Technology, Thesis, Sep. 1990 (believed to be catalogued on or after Sep. 19, 1990) in 219 pages.

Jonic et al., "Three Machine Learning Techniques for Automatic Determination of Rules to Control Locomotion," IEEE, Transactions on Biomedical Engineering, vol. 46, No. 3, Mar. 1999, pp. 300-310.

Kidder et al., "A System for the Analysis of Foot and Ankle Kinematics During Gait," IEEE Transactions on Rehabilitation Engineering, vol. 4, No. 1, Mar. 1996, pp. 25-32.

Kirkwood et al., "Automatic Detection of Gait Events: A Case Study Using Inductive Learning Techniques," Journal of Biomedical Engineering, vol. 11, Nov. 1989, pp. 511-516.

Kirsner, Scott; "A Step in the Right Direction Biomedical Horizons Expanding," Boston Globe, Mar. 17, 2003, pp. 4.

(56) References Cited

OTHER PUBLICATIONS

Kostov et al., "Machine Learning in Control of Functional Electrical Stimulation Systems for Locomotion," IEEE Transactions on Biomedical Engineering, vol. 42, No. 6, Jun. 1995, pp. 541-551.

LaFortune, Mario A.; "Three Dimensional Acceleration of the Tibia During Walking and Running," Journal of Biomechanics, vol. 24, No. 10, 1991, pp. 877-886.

Lee et al., "Activity and Location Recognition Using Wearable Sensors," Pervasive Computing, Jul.-Sep. 2002, pp. 24-32.

Lelas et al., "Hydraulic Versus Magnetorheological-Based Electronic Knee Prostheses: A Clinical Comparison," Massachusetts, 2004, pp. 1-16.

Light et al., Skeletal Transients on Heel Strike in Normal Walking with Different Footwear, Journal of Biomechanics, vol. 13, 1980, pp. 477-480.

Luinge, H.J.; "Inertial Sensing of Human Movement," University of Twente, Netherlands, Thesis, Oct. 30, 2002 in 88 pages.

Martens, W.L.J.; "Exploring Information Content and Some Application of Body Mounted Piezo-Resistive Accelerometers," In P.H. Veltink, & R.C. van Lummel (Eds.), Dynamic analysis using body fixed sensors, Second World Congress of Biomechanics, Amsterdam, 1994, pp. 9-12. Asserted by iWalk in Civil Action No. 12-CV-11061 FDS to constitute prior art to U.S. Pat. Nos. 7,431,737 and 7,896,927. *Applicant requests that the Examiner to consider this reference as qualifying as prior art to the present application, but reserves the right to challenge the reference's prior art status at a later date.*

Mayagoitia et al., "Accelerometer and Rate Gyroscope Measurement of Kinematics: An Inexpensive Alternative to Optical Motion Analysis Systems," Journal of Biomechanics, vol. 35, 2002, pp. 537-542.

McNealy et al., Effect of Prosthetic Ankle Units on the Gait of Persons with Bilateral Trans-Femoral Amputations, Prosthetics and Orthotics International, 2008 32:111.

Moe-Nilssen, R.; "A New Method for Evaluating Motor Control in Gait Under Real-Life Environmental Conditions. Part 1: the Instrument" Clinical Biomechanics, vol. 13, 1998, pp. 320-327.

Moe-Nilssen, R.; "A New Method for Evaluating Motor Control in Gait Under Real-Life Environmental Conditions. Part 2: Gait Analysis" Clinical Biomechanics, vol. 13, 1998, pp. 328-335.

Morris, J.R.W.; "Accelerometry—A Technique for the Measurement of Human Body Movements," Journal of Biomechanics, vol. 6, 1973, pp. 729-736.

Murray et al., "Walking Patterns of Normal Men," The Journal of Bone and Joint Surgery, vol. 46-A, No. 2, Mar. 1964.

Nakagawa, Akio; "Intelligent Knee Mechanism and the Possibility to Apply the Principle to the Other Joints," Proceedings of the 20th Annual International Conference of the IEEE Engineering in Medicine and Biology Society, vol. 20, No. 5, Dec. 1998, pp. 2282-2287.

Otto Bock's C-Leg, see http://web.archive.org/web/20040215152410/http:/www.ottobockus.com/products/lower_limb_prosthectics/c-leg.asp. Asserted by iWalk in Civil Action No. 12-CV-11061 FDS as known or used in this country before Jul. 15, 2004 and on sale in this country more than one year before Jul. 15, 2004. *Applicant request the Examiner to consider this reference as qualifying as prior art to the present application, but reserves the right to challenge the reference's prior art status at a later date.*

Otto Bock®, "C-LEG: A New Dimension in Amputee Mobility," Otto Bock Data Sheet, Otto Bock Orthopadische Industrie, 1997, pp. 4.

Perry, Jacquelin MD, "Gait Analysis:Normal and Pathological Function," Ch. 4, pp. 51-53, 85-87, 1992.

Petrofsky et al., "Feedback Control System for Walking in Man," Computers in Biology and Medicine, vol. 14, No. 2, pp. 135-149, 1984.

Popovic et al., "Control Aspects of Active Above-Knee Prosthesis," International Journal of Man-Machine Studies, vol. 35, No. 6, Dec. 1991, pp. 751-767.

Popovic et al., "Optimal Control for an Above-Knee Prosthesis With Two Degrees of Freedom," Journal of Biomechanics, vol. 28, No. 1, 1995, pp. 89-98.

Raggi et al. Wearable Sensors for the Real-Time Assessment of Gait Temporal Symmetry in Above-Knee Amputees: The 'SEAG' Protocol, Abstracts of the 2007 SIAMOC Congress.

Raggi et al., Gait Analysis Through Inertial Sensors in Transfemoral Amputees: Step and Stride Regularity, SIAMOC 2006 Congress Abstracts/Gait & Posture.

Reitman et al., "Gait Analysis in Prosthetics: Opinions, Ideas, and Conclusions," Prosthetics and Orthotics International, vol. 26, 2002, 50-57.

Robinson et al., "Series Elastic Actuator Development for a Biomimetic Walking Robot," MIT Leg Laboratory, 1999, pp. 1-8.

Robinson, David William; "Design and Analysis of Series Elasticity in Closed-Loop Actuator Force Control," Massachusetts Institute of Technology, Thesis, Jun. 2000 in 123 pages.

Sekine et al., "Classification of Waist-Acceleration Signals in a Continuous Walking Record," Medical Engineering & Physics, 2000, pp. 285-291.

Sin et al., "Significance of Non-Level Walking on Transtibial Prosthesis Fitting with Particular Reference to the Effects of Anterior-Posterior Alignment," Journal of Rehabilitation Research and Development, vol. 38, No. 1, Jan./Feb. 2001, pp. 1-6.

Smidt et al., "An Automated Accelerometry System for Gait Analysis," Journal of Biomechanics, vol. 10, 1977, pp. 367-375.

"State-of-the-Art Prosthetic Leg Incorporates Magneto-Rheological Technology," Medical Product Manufacturing News, Nov. 2000, p. 42 [Web version attached in 3 pages].

Su et al., The Effects of Increased Prosthetic Ankle Motions on the Gait of Persons with Bilateral Transtibial Amputations, Am. J. Phys. Med. Rehabil., vol. 89, No. 1, Jan. 2010.

Thakkar, Sneha, "Energy Economy Gait Analysis of an Autoadaptive Prosthetic Knee," Massachusetts Institute of Technology, Thesis, Aug. 30, 2002 in 58 pages.

"The Electronic C-Leg® Knee Joint System," Instructions for Use, Otto Bock®, 2002, pp. 30. http://www.ottobockus.com/products/lower_limb_prosthetics/c-leg_instructions.pdf (printed Jul. 20, 2006) Asserted by iWalk in Civil Action No. 12-CV-11061 FDS to constitute prior art to U.S. Pat. Nos. 7,431,737 and 7,896,927. Applicant requests that the Examiner to consider this reference as qualifying as prior art to the present application, but reserves the right to challenge the reference's prior art status at a later date.

Tomovié et al., "A Finite State Approach to the Synthesis of Bioengineering Control Systems," IEEE Transactions of Human Factors in Electronics, vol. HFE-7, No. 2, Jun. 1966, pp. 65-69.

Tong et al., "A Practical Gait Analysis System Using Gyroscopes," Medical Engineering and Physics, vol. 21, 1999, pp. 87-94.

Tong et al., "Virtual Artificial Sensor Technique for Functional Electrical Stimulation," Medical Engineering & Physics, vol. 20, 1998, pp. 458-468.

Van Den Bogert et al., "A Method for Inverse Dynamic Analysis Using Accelerometry," Journal of Biomechanics, vol. 29, No. 7, 1996, pp. 949-954.

Van Der Kooij et al., "A Multisensory Integration Model of Human Stance Control," Biological Cybernetics, vol. 80, pp. 299-308, 1998.

Van Der Loos et al., "ProVAR Assistive Robot System Architecture," Proceedings of the 1999 IEEE International Conference on Robotics & Automation, Detroit, Michigan, vol. 1, May 1999, pp. 741-746.

Veltink et al., "Detection of Static and Dynamic Activities using Uniaxial Accelerometers," IEEE Transactions on Rehabilitation Engineering, vol. 4, No. 4, Dec. 1996, pp. 375-385.

Veltink et al., "The Feasibility of Posture and Movement Detection by Accelerometry," 15th Annual International Conference of the IEEE Engineering in Medicine and Biology Society, Oct. 28-31, 1993, San Diego, California, pp. 1230-1231.

Wilkenfeld, Ari J, Ph.D.; "An Auto-Adaptive External Knee Prosthesis," Artificial Intelligence Laboratory, MIT, Sep. 2000, pp. 3.

(56) References Cited

OTHER PUBLICATIONS

Wilkenfeld, Ari J, Ph.D.; "Biologically Inspired Autoadaptive Control of a Knee Prosthesis," Massachusetts Institute of Technology, Thesis, Jul. 2000, (believed to be catalogued on or after Oct. 23, 2000) in 106 pages.
Willemsen et al., "Automatic Stance-Swing Phase Detection from Accelerometer Data for Peroneal Nerve Stimulation," IEEE Transactions on Biomedical Engineering, vol. 37, No. 12, Dec. 1990, pp. 1201-1208.
Willemsen et al., "Real-Time Gait Assessment Utilizing a New Way of Accelerometry," Journal of Biomechanics, vol. 23, No. 8, 1990. pp. 859-863.
Williamson, Matthew M.; "Series Elastic Actuators," Massachusetts Institute of Technology Artificial Intelligence Laboratory, A.I. Technical Report No. 1524, Jan. 1995, pp. 1-83.
Woodward et al., "Skeletal Accelerations Measured During Different Exercises," Proceedings of the Institution of Mechanical Engineers, Part H, Journal of Engineering in Medicine, vol. 207, No. 2, Jun. 1993, pp. 79-85.
Wu et al., "The Study of Kinematic Transients in Locomotion Using the Integrated Kinematic Sensor," IEEE Transactions on Rehabilitation Engineering, vol. 4, No. 3, Sep. 1996, pp. 193-200.
International Search Report in International Application No. PCT/CA2008/000110, dated May 7, 2008 in 4 pages.
International Preliminary Report on Patentability and Written Opinion in International Application No. PCT/CA2008/000110, dated Jul. 21, 2009 in 7 pages.
Office Action in Australian Patent Application No. 2005215769 dated Apr. 6, 2010.
International Search Report and Written Opinion in PCT Application No. PCT/US2011/054043, dated Jan. 26, 2012.
International Search Report in International Application No. PCT/CA2003/000937 dated Dec. 3, 2003 in 4 pages.
International Search Report in International Application No. PCT/CA2003/001120 dated Mar. 2, 2004 in 5 pages.

\* cited by examiner

PROSTHETIC AND ORTHOTIC DEVICES AND METHODS AND SYSTEMS FOR CONTROLLING THE SAME

CROSS-REFERENCE TO RELATED APPLICATION

The present application is a divisional of U.S. application Ser. No. 13/248,532, filed Sep. 29, 2011, entitled "PROSTHETIC AND ORTHOTIC DEVICES AND METHODS AND SYSTEMS FOR CONTROLLING THE SAME," which claims priority to U.S. Provisional Application No. 61/387,888, entitled "INFERENCE LAYER CONTROL SYSTEMS AND METHODS FOR PROSTHETIC AND ORTHOTIC APPLICATIONS," filed Sep. 29, 2010, the entirety of which is hereby incorporated by reference.

FIELD OF THE INVENTION

Embodiments disclosed herein generally relate to motorized prosthetic and/or orthotic devices (PODS) and control systems and methods for operating the same.

BACKGROUND

Prosthetic and orthotic devices for restoring or replacing lost lower-limb functions have been available for many years. Until recently, both types of devices were found as purely mechanical linkages making advantageous usage of simple mechanisms in order to preclude knee buckling in level walking stance phase, while still ensuring some form of swing motion during the aerial phase. While this type of device was shown to be fairly efficient in restoring the structural aspects of the lower-limb role in gait, their incapacity to properly sustain the wide variety of lower-limb dynamics associated with the various gait locomotion activities performed on a daily basis appeared as a sufficient limitation to sustain the development of more advanced devices.

While significant efforts were directed towards designing more advanced mechanisms allowing easier adjustment, or more progressive action, through pneumatics and hydraulics, the rapid advances in energy storage and computer technologies soon allowed to extend the realm of capacities associated with typical orthotic and prosthetic devices. Real-time configuration of passive braking devices such as disclosed, for example, in U.S. Pat. No. 5,383,939 and US Patent Application Publication No. 2006/0136072 A1, greatly improved the adaptability of prosthetic devices to user gait specificities or to variations of the environment in which the locomotion tasks are performed. Moreover, these prosthetic devices allowed the addressing of energy dissipative locomotion tasks in a physiologically-compliant manner never seen before. Although showing increased performance and dynamic adaptation with respect to the locomotion tasks being undertaken when compared to their predecessors, this first generation of computer-controlled prosthetic devices still lacked the adaptability and flexibility required to smoothly integrate into users' daily lives.

Integration of computer controls to the prosthetic and orthotic devices brought about changes to the control system in order to link sensory inputs to the dynamically configurable actuator. However, the purely dissipative nature of these devices greatly simplifies the problem as mechanical power exchanges between the user and the device are unidirectional (i.e., user has to initiate all tasks and provide mechanical power).

Latest efforts in the field of advanced orthotic and prosthetic devices, such as disclosed, for example, in US Patent Application Publication No. 2004/0181289 A1, partly resolved some of the limitations observed in the first generation of computer-controlled orthotic and prosthetic devices by providing a fully motorized prosthetic platform, allowing to address all major locomotion tasks, irrespective of their generative or dissipative nature. Requirements for computer-controlled system increased in complexity as the interactions between the user and the prosthetic or orthotic device were no longer solely initiated by the user. Through the use of a two layer control system, the motorized prosthetic or orthotic device allowed to efficiently manage the mechanical power exchange between the user and the device, such that the synergy between user and motorized prosthetic or orthotic device globally benefited the user. Adequate usage of the prosthetic or orthotic device capacity to generate mechanical power was observed to lead to increased gait quality and activity levels.

Nevertheless, the use of strict state machines to implement the artificial intelligence engine as the highest layer of the prosthetic or orthotic device control system is observed to impose a certain formalism on the manner in which the user executes typical locomotion tasks. While generating a certain learning burden on the user side, the use of firm triggers in order to trigger either distinct state transition or specific joint behavior greatly affects man-machine symbiosis. Moreover, limitations associated with the use of a strict state machine artificial intelligence engine when working in a highly variable environment (i.e., external environment and user himself) are well known and quickly show up as robustness issues from a system perspective. Finally, processing associated with the extraction of complex features associated with specific locomotion task detection is also known to generate a latency between measurement of the sensors value and implementation of the actual actions, which is often observed to greatly affect the prosthetic or orthotic device usability and performance.

Furthermore, common prosthetic or orthotic devices lack the ability to properly reproduce natural knee joint behavior and dynamic properties when used in a context that significantly differs from typical locomotion tasks. While generation of proper joint dynamics during cyclical locomotion portions ensure high symbiosis and user benefits, limitations observed in the capacity to reproduce natural joint compliance, or motions, in either non-locomotor or non-cyclical tasks significantly affect orthotic, or prosthetic, device usability and, accordingly, associated user benefits.

SUMMARY

The following disclosure describes non-limiting examples of some embodiments of prosthetic and/or orthotic devices (PODS), control systems for PODS and methods for controlling PODS. Specifically, a control system architecture and associated engines are described that are able to more efficiently sustain limited ambulation, as well as non-cyclical and cyclical gait for users suffering from either amputation of the lower-limb or dysfunction. For instance, other embodiments of the disclosed systems and methods may or may not include the features described herein. Moreover, disclosed advantages and benefits may apply only to certain embodiments of the invention and should not be used to limit the disclosure.

In certain embodiments, an inference layer control system utilizes inertial sensors for prosthetic and orthotic applications. For instance, certain embodiments of the control system can be designed to manage the detection of, and transitions between, locomotion activities in a lower-limb prosthetic and/or orthotic device (POD) configured to support locomotion activities typically associated with daily living. In certain embodiments, the inference layer control system can analyze, in real-time and/or online, a data stream, generate a high-level physical representation of signals associated with the POD operation, detect locomotion activities and inter-activities transitions, trigger the learning layer described below, perform combinations of the same, and the like.

Certain embodiments include a real-time control system that can use relative vertical and horizontal displacements between consecutive foot strikes (e.g., when the POD or a foot member coupled with the POD makes contact with the ground and begins the stance phase), as well as both relative and absolute lower-limb sagittal plane segment angles, to identify and discriminate between major locomotion activities. Such activities, in certain embodiments, can be grouped into four classes: "Fumbling Around," "Forward Progression," "Generation," "Dissipation," and their respective specific modes.

In certain further embodiments, an inertial navigation engine (INE) can be used to estimate (e.g., in real-time) absolute and relative sagittal plane lower-limb segment angles and relative horizontal and vertical displacements between consecutive prosthetic foot strikes. The horizontal and vertical displacements can be calculated for the thigh segment, the shank segment, the POD, the joint segment, an upper segment or lower segment, a foot segment, and the like. Such an engine can advantageously improve performance and conviviality of motorized lower-limb prostheses.

In an embodiment, the INE is provided based on one or more Inertial Measurement Units (IMUS). IMUS can be positioned on the distal part of a shank segment of a lower-limb POD and on the distal part of a thigh segment. Alternatively or additionally, a sagittal plane rate gyroscope can be coupled with the appropriate compatible IMUS. These units can be coupled with appropriate algorithms and signal processing to make the following estimations: lower-limb segment sagittal plane absolute angles with respect to gravity, lower-limb segment sagittal plane relative angles with respect to two or more gait events that can present a significant measure of a given gait characteristic, relative vertical displacement associated with consecutive foot strikes on a POD, and relative horizontal displacement associated with consecutive foot strikes on a POD.

Certain further embodiments can include an inference layer control module for a POD situated between a reactive layer control module and a learning layer module. The inference layer control module can utilize the relative vertical and horizontal displacements between consecutive foot strikes, absolute lower-limb segment angles, joint torque, ground contact detection, and/or segments angular velocities to identify the nature of the current task being performed by the user. The inference layer control module can also include an inference layer controller based on general classes of locomotion behavior, such as, for example, forward progression (FP), dissipation (DIS), generation (GEN), fumbling around (FA), downwards walking (DW), upwards walking (UW), sit-to-stand transfer (STS) and sitting (SIT) modes.

A motorized prosthetic or orthotic device (POD) is described that includes a first segment including a joint member and a second segment coupled with the first segment via the joint member. The POD also includes an actuator and a control system. The actuator is configured to control motion of the second segment relative to the first segment. The control includes a reactive layer which commands and controls motion of the second segment relative to the first segment, and an inference layer. The inference layer is configured to receive an input stream that includes a first set of data accumulated over one or more gait cycles. The first set of data includes one or more measurements of at least one of a vertical displacement associated with the first segment or the second segment, a horizontal displacement associated with the first segment or the second segment, and an angle associated with the first segment or the second segment with respect to gravity. The inference layer is configured to identify a locomotion activity of a user of the POD based at least on the first set of data, and transmit information regarding the locomotion activity to the reactive layer to control motion of the second segment relative to the first segment. In certain embodiments, the first segment is a thigh segment and the second segment is a shank segment.

A method for controlling a motorized prosthetic or orthotic device (POD) of a user is described. The POD includes a first segment including a joint member and a second segment coupled with the first segment via the joint member. The method includes receiving POD data at an inference layer control, wherein the POD data includes one or more measurements of at least one of a vertical displacement of the POD, a horizontal displacement of the POD, and an angle of the POD with respect to gravity. The method further includes determining a current locomotion activity of the user based at least on the POD data, and transmitting information relating to the current locomotion activity to an actuator control.

A control system for controlling a motorized prosthetic or orthotic device (POD) that is actuatable about a joint is described. The control system includes a first inertial measurement unit (IMU) associated with a first segment of a user and configured to collect a first set of data, wherein the first set of data includes one or more measurements of at least one of a vertical displacement of the first segment, a horizontal displacement of the first segment, and an angle of the first segment with respect to gravity and a second IMU associated with a second segment of the lower-limb POD of the user and configured to collect a second set of data, wherein the second set of data includes one or more measurements of at least one of a vertical displacement of the second segment, a horizontal displacement of the second segment, and an angle of the second segment with respect to gravity. The control system further includes an inference layer in communication with the first IMU and the second IMU and configured to receive the first set of data from the first IMU and the second set of data from the second IMU, and identify a locomotion activity of the user based at least on the first set of data and the second set of data.

BRIEF DESCRIPTION OF THE DRAWINGS

The foregoing aspects and many of the attendant advantages will become more readily appreciated as the same become better understood by reference to the following detailed description, when taken in conjunction with the accompanying drawings, where.

DETAILED DESCRIPTION

Figure 1A:
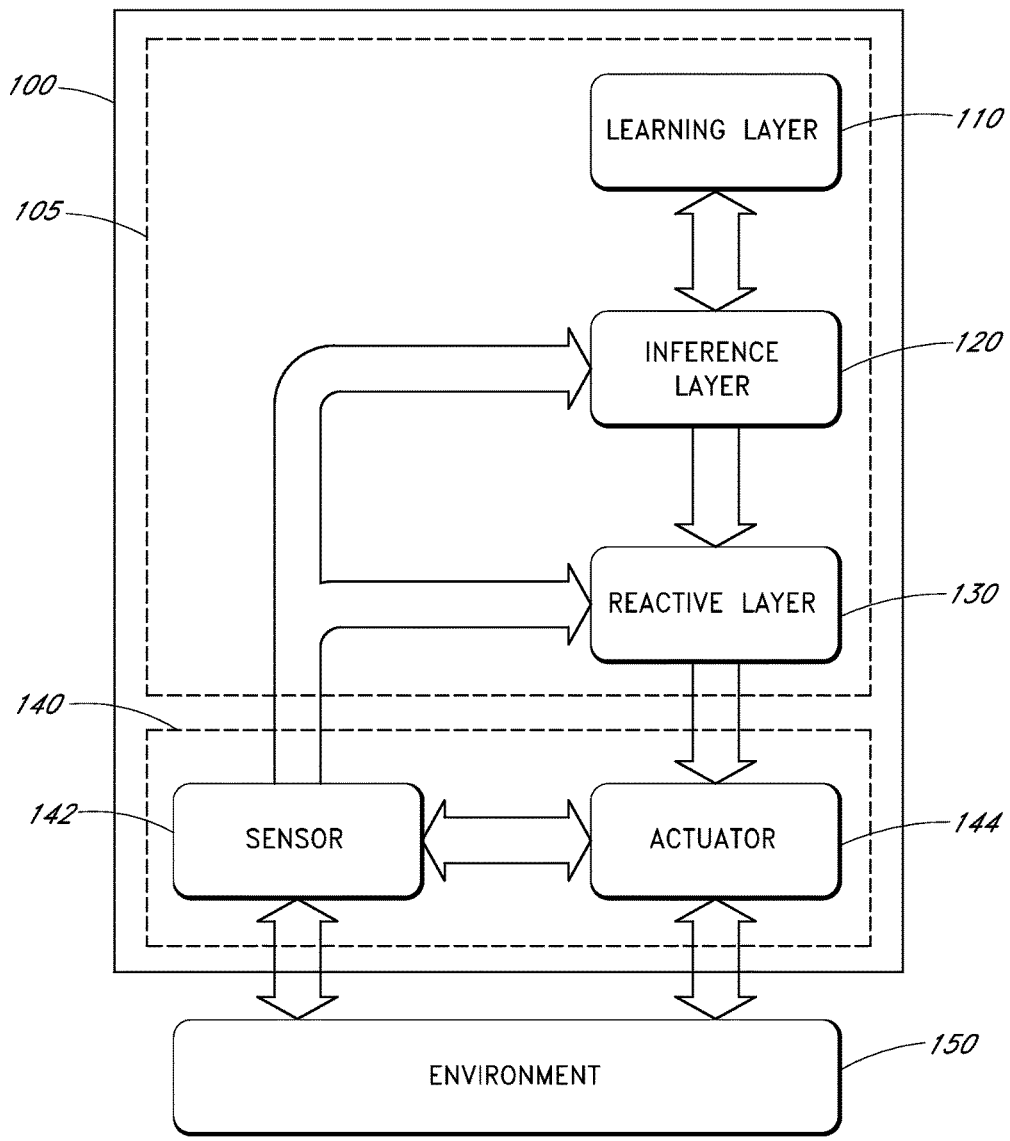
FIG. 1A is a block diagram of the interaction between various controls system layers and building blocks of a motorized prosthetic and/or orthotic device (POD)

The following figures and description provides a detailed description of various embodiments of a control system for use in controlling a prosthetic or orthotic device (POD). In some embodiments, the POD may include a joint and two segments that are actuatable about the joint through the use of a motorized actuator. One example provided below is a motorized, lower-limb prosthesis in the form of a prosthetic knee for use by a trans-femoral amputee. However, the control system described herein can be applied to other types of prosthetics and orthotics as well, such as an ankle or foot POD.

In certain embodiments, the control system includes an inference layer that can be thought of as being loosely modeled on the human ability to respond in a rational, controlled way to external stimuli. To accomplish this, the inference layer can comprise a set of rules and a parameter management system. The rule set can determine both what and when parameters stored in a parameter management system are used. If the POD is properly tuned, the inference layer's rule set can choose performance-enhancing parameters specific to the user's desires in an ever-changing environment.

In certain embodiments, the rule set includes two subsets of rules. The first subset can be used to perform data analysis similar in nature to the comprehension aspect of human cognition. The second subset can be used to act on the data and understanding of that data. As an example, in certain embodiments, the POD can infer from its sensors and/or estimators that it is in contact with the ground. This information, in combination with other inputs, can cause the POD to stiffen in order to prevent the knee from collapsing under the user's weight. Thus, the first set of rules can be thought of as interpreting and understanding stimuli from the environment, while the second set of rules can be thought of as providing a method and/or mechanism to act or react in an appropriate manner based on that understanding of the environment.

In certain embodiments, the parameter management system can update the rest of the POD control system with appropriate parameters based on the decisions made by the rule set. In effect, the management system can include a parameters database and parameters manager that includes the ability to pass data to other parts of the control system.

In certain embodiments, the inference layer can be defined as the second of three layers comprising the overall system. In such embodiments, the first layer (reactive layer) commands and controls the POD's behavior in the desired manner, while the third layer (learning layer) analyzes the device's performance and makes adjustments depending on how well the device is performing. As such, the inference layer can act as a buffer between the first and third layers, only asking for assistance from the third, or learning layer, and only commanding the first, or reactive layer, as desired.

Advanced mechanical prosthetics can be advantageous over a more active, dynamic user because they can offer users a wide variety of potential performance characteristics. These devices can be limited, however, in how they attain these different performance characteristics. Traditionally, these adjustments were made manually. The inference layer described herein can make these adjustments in real-time according to estimations of absolute and relative angles and horizontal and vertical displacements based on data it receives from an array of sensors and estimators. The absolute angles correspond to angles with respect to gravity. The relative angles and displacements correspond to a change in angles and displacements with between events, such as foot strikes.

Organizing the system in such a fashion can be advantageous from an architectural point of view for several reasons. The first is code organization. By conceiving of the system in such a fashion, it is possible to organize the programming logic and code such that each layer is completely encapsulated and separate from the other layers. This can be advantageous because, for example, the layer that runs the motor control algorithm and guarantees stable and predictable system behavior can be completely separated from higher-level decision-making layers. In turn, this can help prevent possible errors made by higher-level layers from trickling down the system hierarchy and adversely affecting the performance of lower-level layers. Another advantage of this organization is that, should each layer become so advanced as to require its own separate processor, reorganizing the system to work on multiple processors can be less complex because the different modules are already implemented as discrete functions. Furthermore, this method of organization can make it easier to expand the prosthetic's capabilities, since only specific portions of the software are modified, as opposed to extensively modifying the entire software system. Moreover, this organizational approach can reduce the burden sustained by the processor(s), since higher-level functions are only executed when lower-level functions require their input. In other words, code is executed only when necessary. Finally, this framework can simplify the development of bionic systems, since it distinguishes real-time processes from event-based processes while also clearly highlighting the nature of the data stream.

Control System Layering

Certain embodiments described herein possess the organization of the control system of a POD 100, as presented in FIG. 1A. This organization of software processes, data streams, and a priori knowledge is commonly known as a multi-layer hierarchical architecture. This method of architectural organization can satisfy at least two objectives, namely provide high performance control of a motorized prosthesis or orthosis, and efficiently organize processes and data stream(s) such that information received from the prosthetic's sensors propagates through the system in an orderly and logical fashion.

The learning layer 110, the inference layer 120, and the reactive layer 130 in FIG. 1A depict the hierarchical layering of the control system architecture 105 of a POD 100. Moreover, the sensors 142, actuator 144, and environment 150 highlight the interactions between the control system 105 and the environment in which the POD 100 operates. Certain embodiments described herein relate to the second level in the control structure hierarchy, namely, the inference layer 120.

In certain embodiments, the system is organized into hierarchical layers based on an examination of the flow of data into and out of the layers, as well as the interdependencies between layers. Moreover, because the data abstraction level necessary to infer which gait activity is being performed can present a level of uncertainty much higher than that associated with the low-level controller formulation, the creation of separate layers can allow the system to maintain at least a minimal level of low-level functionality, even if the inference layer 120 is unable to make a clear decision due to computation errors, sensor errors, or other uncertainty.

The layer names, data abstraction models, and nature of the data stream associated with certain embodiments are described herein using physiological terms. The three layers that can be used to sustain motorized prosthesis or orthosis operation in certain embodiments include, but are not limited to, a learning layer 110, an inference layer 120, and a reactive layer 130. The different layers can be categorized based on the level of abstraction, the time frame in which they act, etc.

The various layers interact with each other to improve the performance of the POD 100. For example, a well-tuned device may provide reasonable performance using only the reactive 130 and inference layers 120, but may be unable to evolve in order to meet the user's changing needs, or respond to long term changes in the operating environment without the use of a learning layer 110.

The learning layer 110 can include the control structure's highest abstraction level, and can be the level furthest away from raw sensor data. The learning layer 110 can be loosely analogized to human cognitive functions, and it can be used to recursively improve the POD control system's performance as time passes. In addition, the learning layer 110 can have the longest time frame in which it acts. For example, in certain embodiments, the learning layer 110 does not respond to changes in gait pattern between steps. Rather, the leaning layer identifies and responds to long-term trends in user performance.

The learning layer 110 can also define what is considered an improvement in performance. The criteria for improved or reduced performance can evolve with time as the user becomes more familiar with the device and demands a higher level of performance. The evolution of what optimality means can be thought of as the device's transition from a device possessing a moderate level of performance coupled with a very high level of safety to a device possessing a high level of performance coupled with reduced user safety constraints, thereby increasing the device's flexibility and performance potential. As it evolves, the learning layer 110 can also decide to allow user access to features that had previously been hidden or were not made available.

In certain embodiments, the learning layer 110 can comprise an expert system consisting of rule and data sets that can make decisions as to how well the POD performs in particular situations, and use the inference layer 120 to implement the high-level decision making. The learning layer 110 alters the rule set or parameter values used by the inference layer 120 incrementally and over longer periods of time to dictate POD performance.

In addition, the learning layer 110 can provide support as the controller formulation itself may sometimes require change because: 1) a single actuated POD can potentially cover a large and diversified range of locomotion activities, and 2) the user can progressively adapt its behavior, which may require additional adjustment to ensure that the system maintains a stable level of performance.

The inference layer 120 can be responsible for a variety of different activities. These activities can include, but are not limited to, identifying the current activity being performed by the user, measuring the performance of the POD 100, requesting that the learning layer 110 examine a particular performance issue, organizing and passing the requested/required data to the learning layer 110, and providing the reactive layer 130 with enough data to smoothly execute the task at hand.

Within the global POD control system 105, the inference layer's role can be conceived of as mimicking the human brain's conscious decision making process. Using the rules and data it acquires from the learning layer 110, the inference layer 120 can infer which course of action is appropriate from sensory data measurements and estimates. Thus, the inference layer 120 can mimic the human ability to apply what one has learned to specific present and future situations.

Unlike the learning layer 110, the inference layer 120 reacts over the course of a gait cycle. The inference layer 120 can quickly apply rules it has learned from the learning layer 110 to situations as they arise and respond accordingly. For example, the response time of the inference layer 120 can be on the order of tenths of seconds.

Contextually, the inference layer 120 can be thought of as an intermediate data abstraction level, where most of the work consists of extracting features from an input stream comprising pre-processed data. The data can be processed and characterized to achieve objectives including, but not limited to, managing the POD 100 such that system behavior matches the activity being undertaken by the user and quantifying system performance in terms of overall functionality of the device.

The intermediate position the inference layer 120 occupies within the hierarchy can serve an additional purpose: protecting the reactive layer 130 from the learning layer 110. That is, the inference layer 120 can prevent the learning layer 110 from changing parameters directly used by the reactive layer 130, which may lead to system instability. Instead, the learning layer 110 can suggest that the inference layer 120 take a particular action or slightly alter a variable in a data set.

The reactive layer 130, in certain embodiments, represents the lowest abstraction level of the control structure. The reactive layer 130 can directly enforce the desired behavior that is responsive to the activities undertaken by the user. Here, the desired behavior can be determined by the inference layer's rule set, which the learning layer 110 can alter.

In other words, similar to the general behavior of the human arc-reflex, the reactive layer 130 of certain embodiments can immediately enforce a predefined behavior based on a reduced set of sensory input and estimates. The time frame for the operation of the reactive layer 130 can be on the order of milliseconds. More specifically, the reactive layer 130 can handle the motor control laws of the prosthetic system.

Although the control system architecture presented in FIG. 1A may appear to hierarchical in nature, the system can have a parallel in structure by allowing the reactive layer 130 to manage itself. For example, in certain embodiments, the reactive layer 130 can use a knee torque sensor output to implement a low-level impedance controller to manage the system's actuator behavior in real-time. Alternatively, the same knee torque sensor output can be used by the inference layer 120 to detect the occurrence of a transition in the user's gait activity to downwards walking. Both decisions present different levels of complexity can be made independently by the different control layers.

Additional details regarding control layers useable with certain embodiments of the invention are disclosed in U.S. Publication No. 2011/0125290 A1 and in International Patent Application No. PCT/CA2008/000110, titled "Reactive Layer Control System for Prosthetic and Orthotic Devices," filed on Jan. 21, 2008, and published as WO 2008/086629 A1 on Jul. 24, 2008, the disclosures of which are incorporated herein by reference in its entirety.

Configuring the inference layer control system based on these three rationales is motivated by the possibility that there may be no single control system formulation that can respond to all user needs associated with an actuated POD 100 in all situations.

Figure 1B:
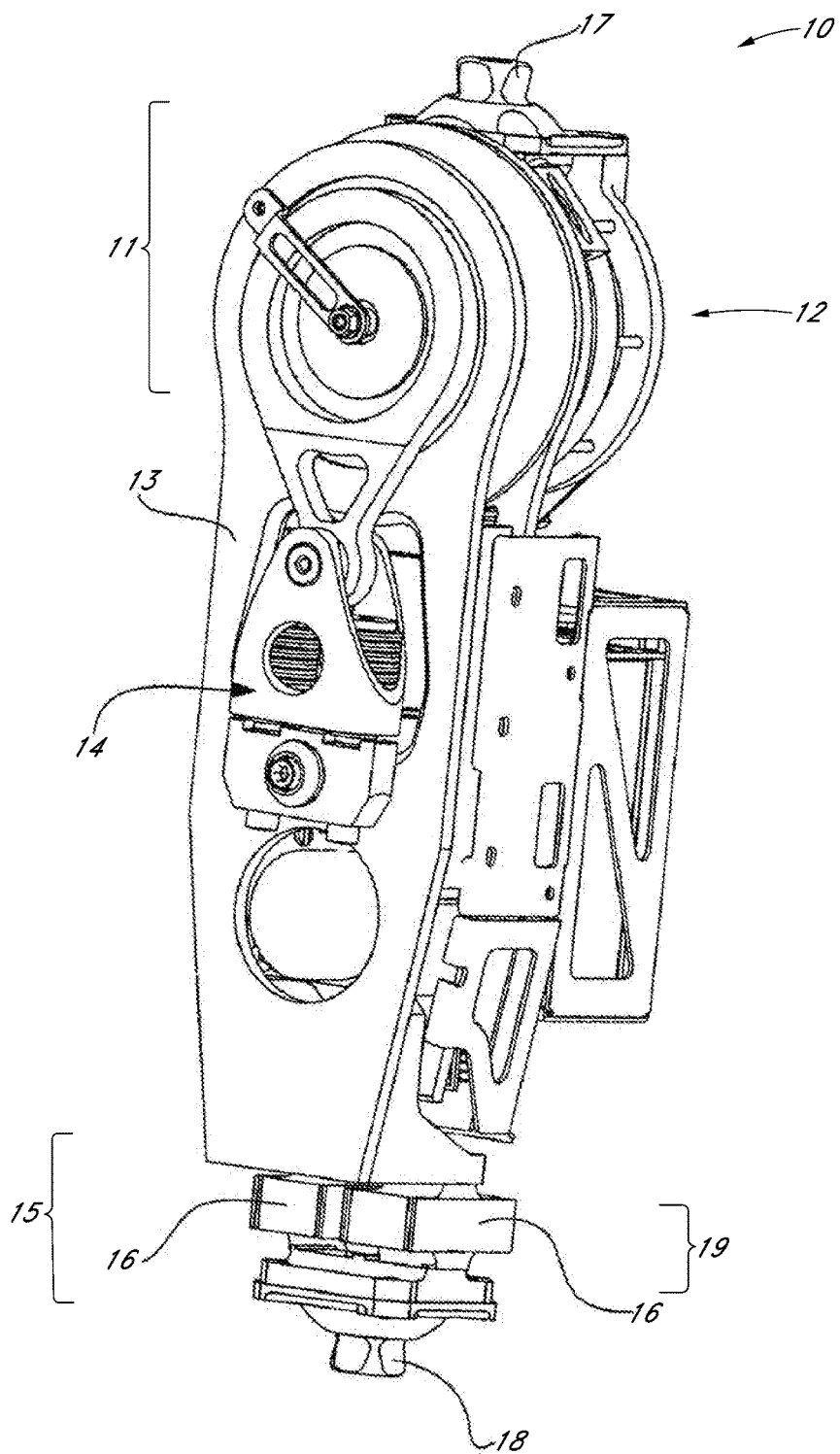
FIG. 1B is a schematic diagram depicting an embodiment of a motorized prosthetic and/or orthotic device.

FIG. 1B is a diagram illustrating an embodiment of a lower-limb POD 100 in the form of a motorized knee prosthesis 10, further details of which are described in U.S. Publication No. 2009/0299480 A1, the entirety of which is hereby incorporated by reference. The prosthesis 10 includes a proximal connector 17 sitting on top of an actuator 12 which is axially mounted at the knee joint 11 level. The proximal connector is configured to be connected to a socket (not shown) that is mountable to the leg stump, e.g., a thigh, of a user. The socket can be placed over or around the leg stump, or be grafted to the tissue of the user. The proximal connector 17, the actuator 12, and the knee joint level 11 can form a thigh segment of the prosthesis 10.

A shank segment of the prosthesis 10 can include a shank structure 13, such as a tibial member extending downward from the proximal connector that is rotatable via the actuator 12 relative to the proximal connector 17. In this example, the actuator 12 may be, for example, a DC brushless motor serially connected to a reduction mechanism. The reduction mechanism of the actuator 12 allows the conversion of the motor high-speed low torque output characteristics into a low-speed high-torque output that is more coherent with the requirements associated with the human knee joint role in most commonly encountered locomotor tasks. A second transmission stage is then provided in order to connect the reduction mechanism output to the shank structure 13 of the motorized knee prosthesis 10. This second transmission stage is composed of a compliant linkage 14, allowing both measurement of the net torque present at the interface between the shank structure 13 and the actuator 12 output and high-efficiency level walking stance flexion energy storage and return.

The motorized knee prosthesis 10 also includes sensors to sustain the multi-layered controller 105 (see FIG. 1A). The sensors can be inertial measurement units (IMUS) and can include accelerometers, gyroscopes, kinematic sensors, torque sensors, and the like. A first sensor (not shown) can be included in the transmission assembly of the actuator 12 such that the relative position between the user thigh segment and the reduction mechanism output can be measured in real-time. Net torque present at the interface between the shank structure 13 and the actuator 12 output can be measured through the deflection of the compliant linkage 14 transmitting motion between both parts 12 and 13, using a second sensor (not shown) mounted in the transmission assembly of the actuator 12 for that purpose. A load cell assembly 19 containing one or two load cells 16 can be located at the distal shank portion 15 between the shank structure 13 and the distal connector 18 of the motorized knee prosthesis 10 to quantify the load found in the distal shank portion 15. The distal connector 18 is configured to connect to a prosthetic ankle or foot (not shown). The sensors can be located in any number of locations and fewer or additional sensors can be used. For example, the prosthesis 10 can include only one sensor located in either the thigh segment or the shank segment. Furthermore, the sensors can be located in any number of different locations on the thigh segment or the shank segment. In an embodiment, one sensor is located on the thigh segment and another sensor is located on the shank segment. In an embodiment, the sensors are located on a distal portion of the segments so as to be closer to the ground when the user is in a stance position.

It is to be understood that although the motorized knee prosthesis 10 described above has been given as an example of the motorized prosthetic or orthotic apparatus 140, the multi-layered controller 105 may be similarly used with other motorized prostheses or orthoses having general characteristics similar to that of the motorized knee prosthesis 10. More specifically, the multi-layered controller 105 may be similarly used with a POD 100 having sensors for measuring the net torque of its actuator output, sensors for detecting ground contact and sensors for measuring the position of the actuator.

Inference Layer

As previously discussed, the inference layer 120 in the POD control system architecture 105 can be used for a variety of purposes, including, but not limited to, analyzing the data stream provided by the measurement units and generating a high-level representation of measured physical quantities so that the inference layer 120 can infer which activity the user is currently performing and detect inter-activity transitions, define the behavior of the reactive layer 130 by modifying the parameters of the control algorithm in response to the detected gait activity, and monitor system performance and trigger the learning layer 110, so that the learning layer 110 can analyze system performance and propose changes to the data and rule sets of the inference layer 120.

In certain embodiments, the main responsibility of the inference layer 120 control system from the viewpoint of the overall system is to infer the nature of the activity the user is currently performing, as well as to detect the occurrence of a possible transition to another activity. In certain implementations, the locomotion activities of the inference layer control system 120 can be divided into types, including, but not limited to, fumbling around (FA), forward progression (FP), dissipation (DIS), and generation (GEN).

The FA type of activity can correspond to any non-locomotor ambulation being performed by the user. The FA activity can be thought of as a general umbrella term covering movements associated with standing-up, lateral ambulation, backward ambulation, or any other motion that cannot be clearly identified through the presence of strong forward-oriented body dynamics. The FA activity can also represent the default system state, as this can provide a neutral behavioral state which favors safety over high performance dynamics.

The FP activity can correspond to locomotor ambulation where strong forward dynamics can be found, and can be associated with a level walking gait. Within this context, use of a separate activity type for locomotor and non-locomotor gaits can allow the control system to independently manage these activities, since these two types of activities can be significantly different in nature compared to other gait activities.

The DIS activity type can be used for ambulation where the POD actuator removes energy from the system in a controlled manner. During the DIS activity, the lower-limb prosthesis can slowly flex against an external force (typically the user's body weight). This can be used to control the velocity of the user's body weight during stair and steep inclined plane descent.

The GEN activity type can be used for ambulation where the POD 100 injects mechanical power to move the user's body weight, such that overall progression of movement can be sustained. This can be used to push an active user up stairs or steep inclined planes.

Along with the general types of locomotion activity described above, additional specialized forward progression modes and specialized fumbling around mode can be defined. The specialized forward progression modes can include, but are not limited to, downwards walking (DW) and upwards walking (UW). The specialized fumbling around modes can include, but are not limited to, sitting down and (SIT) and sit-to-stand (STS) mode.

This DW mode can fulfill specific gait requirements associated with a range of downward inclined planes. In some instances, the FP mode may not allow proper control of gait cadence and the DIS mode may not allow properly sustained forward progression because the knee may become too dissipative. Within that context, the DW mode can be seen as an intermediate level between level walking and stairs descent. Accordingly, the POD behavior can be adapted to reorient the direction of the user's progression to match the incline of the surface or ground.

The UW mode can fulfill specific gait requirements associated with the range of various upward inclined planes. In some instances, the FP mode may not allow proper weight transfer over the prosthetic limb and the GEN mode may not allow properly sustained overall progression. Within that context, the UW mode can act as an intermediate level between level walking and stairs ascent. Accordingly, the POD behavior can be adapted to reorient the direction of the user's progression to match the incline of the surface or ground.

The STS mode can be associated with specialized behavior for sit-to-stand and stand-to-sit transfers. While this FA mode is primarily devoted to the management of these non-locomotor movements, it can also be used for other tasks showing similar requirements, such as kneeling, squatting, or other similar activities.

The SIT mode can be associated with specialized behavior for proper prosthetic and/or orthotic device operation while the user is seated. Although this feature is primarily used to sustain the specific non-locomotor task of sitting, features associated with this FA mode can also be used in other contexts, such as kneeling for a prolonged period of time or other similar activities.

Each of these locomotion activities can be characterized by a set of parameters stored in a parameters database, discussed in greater detail below with reference to FIG. 4, and can be used to configure the reactive layer control engine reactive layer 130 so that the POD's behavior can be configured to support the task being performed by the POD's user.

Figure 2:
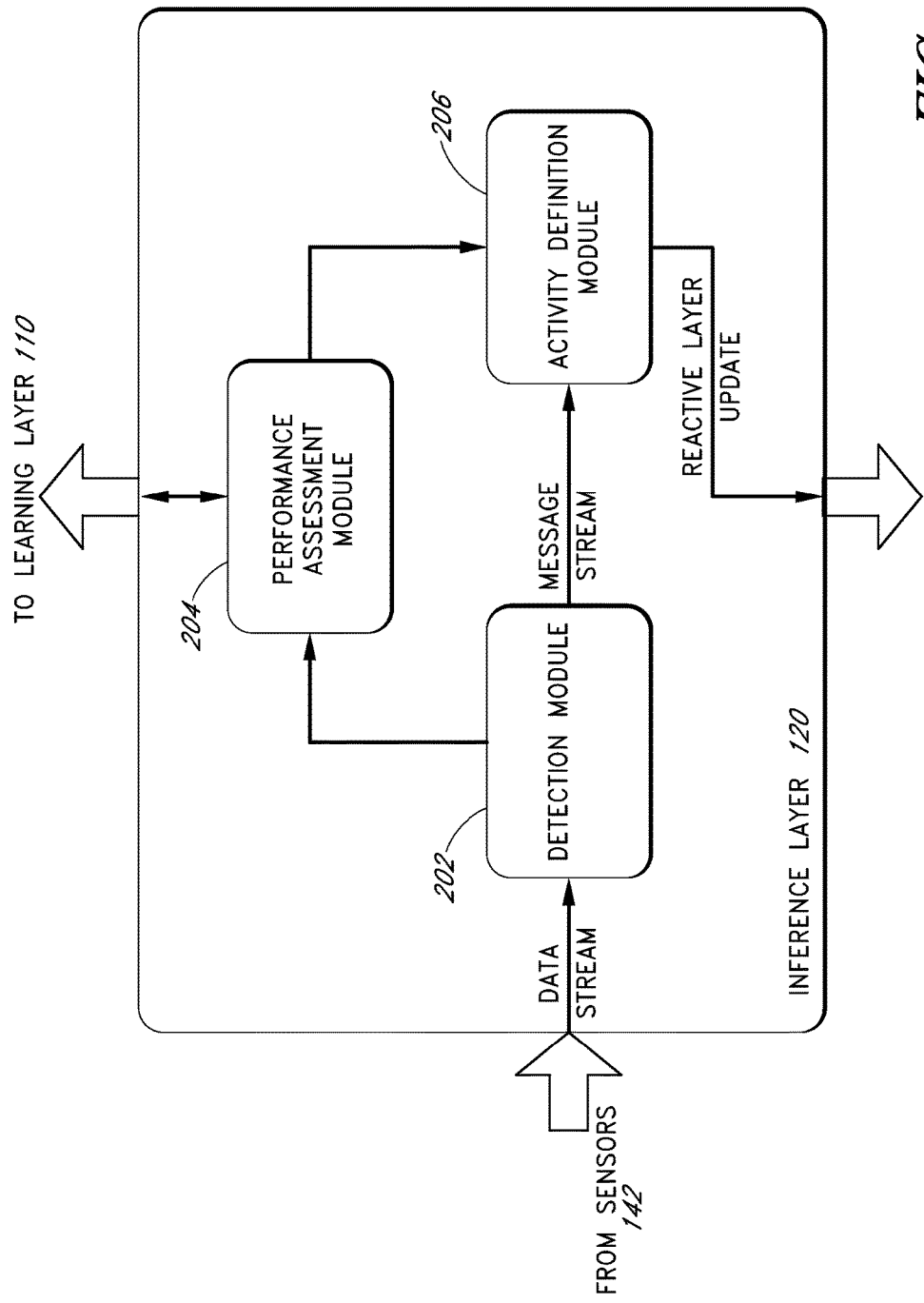
FIG. 2 is a block diagram depicting an illustrative inference layer control system of a POD.

FIG. 2 is a block diagram illustrating various components associated with the inference layer control system 120. As illustrated, the inference layer 120 includes a detection module 202, a performance assessment module 204, and an activity definition module 206. The detection module 202 receives a data stream from sensors, processes the data, and then transmits relevant data to the performance assessment module 204 and/or the activity definition module 206. The performance assessment module can also transmit information to the activity definition module 206. The activity definition module 206 transmits relevant updates to the reactive layer 130.

The detection module 202 can process the sensor data stream for the inference layer control system 120 in order to extract features of interest, which can then be used to identify the locomotion activity the user is currently performing. The detection module 202 can use one or more estimators to generate a number of different estimator messages, which can be transmitted to the activity detection module 206 for processing. Additional details with respect to the detection module 202 will be described below with reference to FIG. 3.

The performance assessment module 204 can be configured to evaluate system performance based on actual parameters specific performance models. The parameters can be found in the parameter database or received from the detection module 202. The performance assessment outcome can be fed to the learning layer 110 of the POD control system 105, which can provide parameter updates to the inference layer's parameter database. By providing parameter updates to the database, the learning layer 110 can improve system performance in compliance with the specific needs of the user of the POD 100.

The activity definition module 206 can use information received from the detection module 202 and the performance assessment module 204 to infer an appropriate course of action to take using an arbitration mechanism. The various actions associated with the arbitration mechanism can include, but are not limited to, switching to a new activity, adopting a fallback behavior to ensure user safety, maintaining the current activity, or other suitable activities. Additional details with respect to the activity definition module 206 will be described below with reference to FIG. 4.

Figure 3:
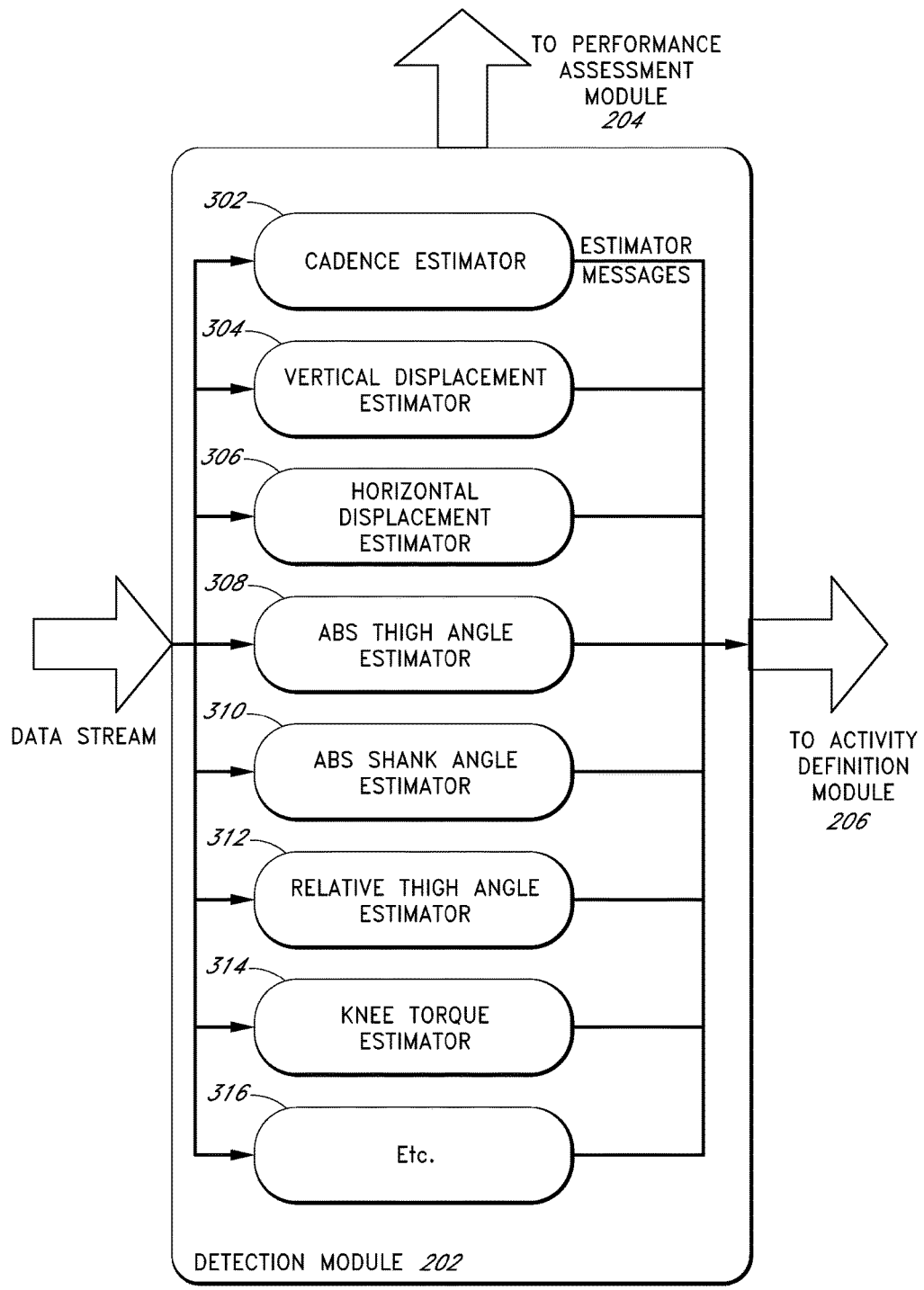
FIG. 3 is a block diagram depicting an illustrative detection module of an inference control system.

In certain embodiments, the inference layer control system 120 processes the sensor data stream using the detection module 202 to extract features of interest, which can then be used to identify the locomotion activity the user is currently performing. FIG. 3 is a block diagram illustrating an embodiment of the detection module 202. The detection module 202 includes various estimators 302-316, which are used to process the raw data stream. Based on the output of the various estimators 302-316, the detection module 202 generates estimator messages for the activity detection module of FIG. 4.

As illustrated in FIG. 3, the detection module 202 can include a cadence estimator 302, a vertical displacement estimator 304, a horizontal displacement estimator 306, an absolute thigh angle estimator 308, an absolute shank angle estimator 310, a relative thigh angle estimator 312, a knee torque estimator 314, and the like. Each estimator can be used to estimate different attributes of the POD 100 and POD user during use. For example, the cadence estimator 302 can estimate the current cadence of the POD user by measuring the duration of swing phase and stance phase between events, such as foot strikes. The vertical displacement estimator 304 can estimate the vertical displacement of the thigh segment, shank segment, upper or lower segment, POD, foot, heel and/or toe using the sensor data. The horizontal displacement estimator 306 can estimate the horizontal displacement of the thigh segment, shank segment, upper or lower segment, POD, foot, heel and/or toe using the sensor data. The absolute thigh angle estimator 308 can estimate the absolute thigh angle of the POD user based on the sensor data. The absolute shank angle estimator 310 can estimate the absolute shank angle of the shank based on data received from the IMUS. The relative thigh angle estimator 312 can estimate the relative thigh angle based on the sensor data. The knee torque estimator 314 can estimate the knee torque throughout the gait cycle using a torque sensor. Additional estimators can be used in accordance with the targeted prosthetic device or the desired type and extent of locomotion activities to be supported. In addition, estimators can be selected that are closely related to the basic components of the locomotion activities. Furthermore, in certain embodiments, a parallel estimation structure may be preferable over other types of approaches, as it can provide a comprehensive data set to the activity detection module 206 each time the estimators are used. While the reactive layer 130 can make use of sensor data in its most raw form without performing any transformations on it, the inference layer detection module 202 can take the raw data stream and process it such that higher level information can be extracted from it.

In an embodiment, the data can be supplied by an inertial navigation engine (INE). The INE can merge raw signals issued from inertial measurement units (IMUS) to generate a high-level representation of physical phenomena affecting the lower-limb POD 100. These measurements can include changes in both sagittal plane absolute and relative segments angles, as well as the relative displacement of the POD 100 during consecutive foot strikes on a walking surface. As such, in certain embodiments, an INE can be used to implement the inference layer control system 120 of the POD 100. It should be noted, however, that the inference layer control system 120 need not rely on an INE, but rather can directly rely on inertial sensor data streams.

Additionally, estimators 302-316 used in the operation of a POD inference layer detection module 202 can be more simple than an INE. Simple estimators can also be useful and relevant in the execution of complex decision processes performed by, other mechanisms, such as the arbitration mechanism discussed in greater detail below with reference to FIG. 4.

In certain embodiments, the estimators 302-316 continuously process data issued from sensors located in the system while looking for specific physical phenomena. These physical phenomena can take various forms depending on the nature of the physical representation generated by the estimator. In some embodiments, simple estimators can recognize physical phenomena via an actual value comparison against a fixed threshold value, while in other embodiments more complex estimators can recognize physical phenomena via model-based assessment of the data, such as the user's center-of-mass positioning, etc. Tracking the physical phenomena using a parallel estimator engine can allow the detection module to wake up the activity definition module 206 whenever an estimator encounters data requiring further assessment. In this way, the activity definition module 206 can be activated only when relevant information is available, thus using less processing power and increasing efficiency.

As mentioned above, the INE can act as the core engine sustaining the majority of the estimators in the detection module 202. The INE can run in the background, while providing the estimator processes with data to perform basic tasks. The INE can provide a number of estimations and data used in the inference layer control system 120, including, but not limited to, the estimation of the sagittal plane relative vertical displacement of the prosthetic limb between consecutive foot strikes, the estimation of the sagittal plane absolute segment angles, the estimation of the sagittal plane relative segment angles (i.e., angles swept by a given segment between two gait events that is known to present a significant measure of a given gait characteristic), the estimation of the sagittal plane relative horizontal displacement of the prosthetic limb between consecutive foot strikes, and the average outputs of the IMUS.

In addition, the INE can estimate, in real-time, the relative vertical and horizontal displacements associated with consecutive foot strikes of the POD 100 based on forward kinematics of the lower-limb segments by measuring the lower-limb kinematic configuration at foot-off (e.g., when the POD or a foot member coupled with the POD ends contact with the ground and begins the swing phase) and subsequent foot-strike events (e.g., when the POD or a foot member coupled with the POD makes contact with the ground and begins the stance phase), and then computing the resulting difference in vertical and horizontal distance due to the variation in segments angles. For example, the angle of the POD or individual segments at foot-off can be compared with the angle of the POD or individual segments at a subsequent foot strike. The difference between the two angles can be used to determine the relative vertical and horizontal distance. The INE can also merge or combine outputs of the shank, thigh, and forward kinematics navigation solution together to minimize the uncertainty of the relative vertical displacement estimates and improve their accuracy by averaging their respective outputs, weighting those averages, and then using a heuristic decision-making process to establish the most relevant estimate and determine how to apply the weighting.

As an example, and not to be construed as limiting, upon receiving the sensor data the estimators can determine whether the data falls within a predefined range of acceptable values. For example, the horizontal displacement estimator 306 may have an acceptable range of 0-4 ft. If the horizontal displacement estimator 306 receives data indicating a horizontal displacement of >4 ft, the sensor data can be rejected. Once the individual sensor data is verified, the estimators can compared the data received from multiple sensors (when multiple sensors are used). The estimator may have another predefined threshold for measured differences between the sets of sensor data. If the difference is larger than the predefined threshold, the sets of sensor data may be discarded by the estimator. For example, if one set of sensor data indicates a horizontal displacement of 4 ft., and another set of sensor data indicates a horizontal displacement of 1 ft., the horizontal displacement estimator 306 can discard the two sets of data. Once the sets of data are individually verified and verified together, the estimator can merge the sets of data. In an embodiment, the estimator merges the data by averaging the data. However, the data can be merged using alternative methods, such as selecting the set of data that has a high confidence level, etc. Alternatively, the activity definition module 206, described above, can verify the data.

The different estimations can be used by the inference layer control system 120 to determine a locomotion activity of the user. The estimation of the sagittal plane relative vertical displacement of the prosthetic limb between consecutive foot strikes can be used to discriminate whether the POD 100 is operating on a level surface (e.g., walking, standing, or fumbling around), a surface showing a positive slope (e.g., stairs or upwards ramp ascent), or a surface showing a negative slope (e.g., stairs or ramp descent). The estimation of the sagittal plane absolute segment angles (i.e., with respect to the gravity vector) can be used to evaluate the user's upper body position (e.g., center-of-mass) with respect to the prosthetic limb. The sagittal plane absolute segment angles estimate can be used to assess the user's forward progression and/or loss of equilibrium. The estimation of the sagittal plane relative segment angles (i.e., angles swept by a given segment between two gait events that is known to present a significant measure of a given gait characteristic) can be used to optimize the general synchronization between the prosthetic and sound limb segments and joints. The estimation of the sagittal plane relative horizontal displacement of the prosthetic limb between consecutive foot strikes can be used to quantify the distance covered by the user's upper body during that period of time. This sagittal plane relative horizontal displacement data can be analyzed in combination with the relative vertical displacement to estimate the relative slope of the terrain on which the user is operating the device.

In certain embodiments, such angles and displacements can be estimated in real-time by selecting appropriate prosthetic device embedded sensors and coupling them with appropriate algorithms and signal processing. For example, the MicroStrain 3DM-DH (MicroStrain Inc., 459 Hurricane Lane, Suite 102, Williston, Vt., 05495, U.S.A.) is an Inertial Measurement Unit (IMU) that can be used to estimate the outputs listed above. The MicroStrain 3DM-DH device can be configured to provide accelerometer outputs, such as the linear acceleration measured along the three orthogonal axes associated with the body on which the accelerometers are mounted. In addition, the MicroStrain 3DM-DH device can be configured to provide processed pitch, roll, and yaw angle outputs up to a frequency of 45 Hz.

By connecting an IMU device to both the prosthetic lower-limb shank segment and thigh segment, absolute segment angles can be estimated in real-time. Similarly, tracking the provided absolute angle streams can assist in the measurement of relative angles (e.g., swept angles), since gait event recognition can be easily implemented in the software algorithm used to retrieve data from the IMUS.

In certain embodiments, the relative vertical displacement of the prosthetic limb can be estimated based on the absolute angles alone, a combination of the accelerometer signals and absolute angle signals, or a combination of accelerometer signals and segment angular velocities extracted from the absolute angle signals. The appropriate method of estimation can be selected based on the nature of the locomotion activities the control system and/or prosthetic device sustains. In other embodiments, the segment angular velocities can be directly measured using a specific sensor (e.g., an ADXRS-610 rate gyroscope from Analog Devices Inc., 3 Technology Way, Norwood, Mass., 02602, U.S.A.). However, different IMUS may require different hardware configurations.

In certain embodiments, absolute segment angles can be used to estimate the relative vertical or horizontal displacement based on the assumption that actual user center-of-mass displacement during the prosthetic limb swing phase can be insignificant with respect to the relative prosthetic limb displacement being estimated. In that context, estimation of the relative horizontal and vertical displacement from the last prosthetic limb foot-off event to the subsequent foot strike can be based on the prosthetic lower limb kinematics. In addition, in this embodiment, relative horizontal and vertical displacement from the last prosthetic limb foot-off event to the subsequent foot strike can be estimated without integrating the time-based signals because it only considers the resulting difference between two different lower-limb kinematic configurations. Alternative methodologies described below can also be used.

In certain embodiments, the combination of the accelerometer signals and the actual segment absolute angles can be used to track relative vertical and horizontal motion of the lower-limb through double integration of time-based acceleration signals. Thus, for each time period during which accelerations are measured in the segment local coordinate systems, an associated incremental vertical and horizontal displacement can be computed by projecting the incremental displacement onto the vertical-horizontal reference system using the absolute angle value associated with each lower-limb segment. Summing all the incremental displacements in between the foot-off and foot-strike events enables computation of the associated relative displacement in the vertical-horizontal coordinate system (i.e., the sagittal plane). In this way, the inference layer 120 can account for the movement of the user's center-of-mass, and the accelerations associated with this movement can be recorded by the accelerometers and accounted for in the relative displacement estimates.

Similarly, in certain other embodiments, relative vertical and horizontal displacements can be estimated based on acceleration levels measured in the segment local coordinate system summed up over specific periods of the gait cycle. Under this methodology, calibration of an embedded absolute segment angles tracking process can be accomplished by using the absolute angles feedback from specific instants of the gait cycle. This tracking process can be based on periodical calibration of the segments actual absolute angles and dead reckoning, which can be done through integration of the time-based angular velocity signal. The velocity signal can be extracted either from the absolute angle signals or through the addition of a separate angular rate sensor to the hardware previously described.

In certain other embodiments, a forward kinematics estimation of the above mentioned displacements can be carried out in parallel with the prosthetic shank and thigh relative displacement estimation processes to minimize the impact and improve the performance of the double integration of the acceleration signals over time and the forward kinematics estimation. The outputs of both can be merged to reduce the estimated displacement noise level and uncertainty.

Information issued from the detection module 202 can be sent to the activity definition module 206 in the form of event-based messages. The event-base message can be issued whenever a detection module estimator detects the occurrence of a physical phenomenon that is of interest from the viewpoint of the control system. Upon detecting such a phenomenon, the detection module 202 can generate messages containing the output of all estimators and transfer the messages to the activity definition module 206, which can process the messages.

Figure 4:
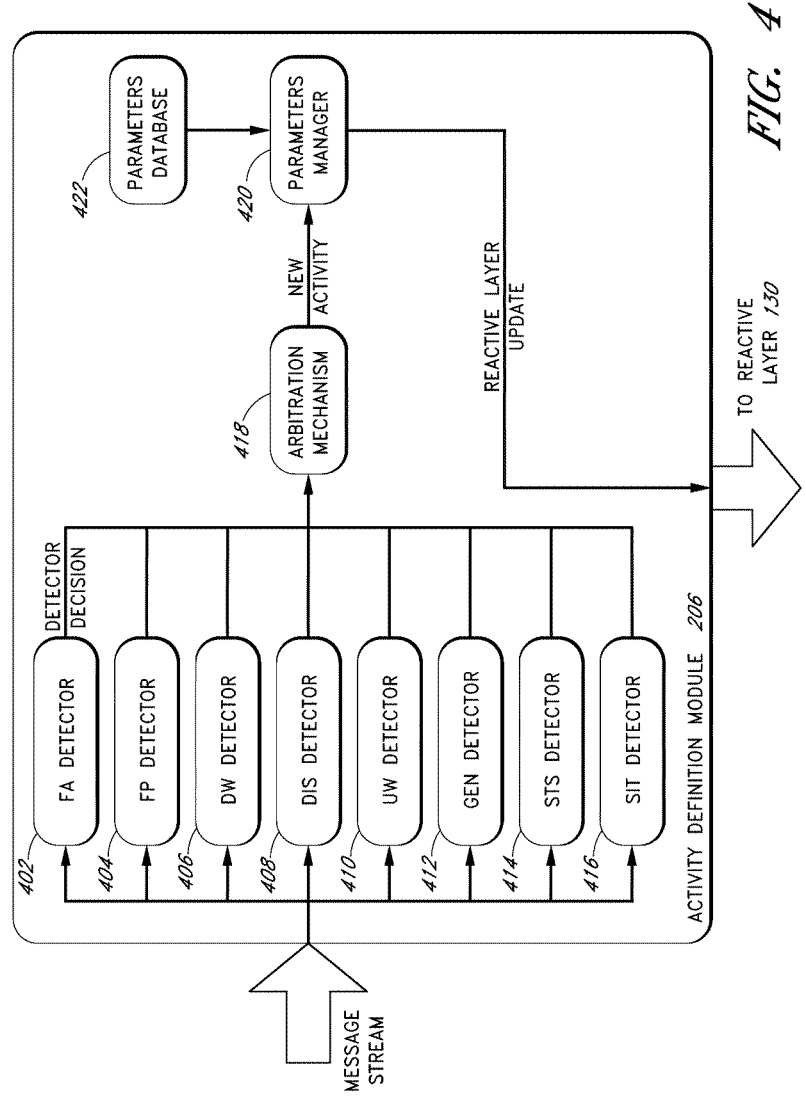
FIG. 4 is a block diagram depicting an illustrative activity definition module of an inference control system.

FIG. 4 is a block diagram illustrating an embodiment of the activity definition module 206. As illustrated, the activity definition module 206 can include one or more locomotion activity detectors 402-416 operating in parallel, an arbitration mechanism 418, a parameters manager 420, and a parameters database 422. The detectors 402-416 can include, but are not limited to, a forward progression (FP) detector 402, a dissipation (DIS) detector 404, a generation (GEN) detector 406, fumbling around (FA) detector 408, a downwards walking (DW) detector 410, an upwards walking (UW) detector 412, a sit-to-stand transfer (STS) detector 414, a sit (SIT) detector 416, and the like. Each detector can use the data from one or more of the estimators to detect an activity. For example, the FP detector can use data from one or more of the cadence estimator 302, the horizontal displacement estimator 306, the absolute an relative thigh angle estimators 308, 312, and the absolute shank angle estimator 310, and a relative shank angle estimator to determine whether the POD is moving forward.

In an embodiment, the FP detector 402 uses data from the cadence estimator 302, the vertical displacement estimator 304, and/or the horizontal displacement estimator 306 to detect forward progression. In another embodiment, the FP detector 402 uses the data from the relative thigh angle estimator 312 and/or a relative shank angle estimator to detect forward progression.

In an embodiment, the DIS detector 404, GEN detector 406, DW detector 410 and UW detector 412 use data from the relative thigh angle estimator 312 and/or a relative shank angle estimator to detect a dissipation activity, a generation activity, a downward activity and/or an upward activity. Each detector may use a different threshold to identify the respective activity. For example, a positive and large relative vertical displacement may indicate an upward activity, such as stair ascent, while a smaller positive relative vertical displacement may indicate a generation activity. Similarly, a smaller negative relative vertical displacement may indicate a dissipation activity and a larger negative relative vertical displacement may indicate a downward activity, such as stair descent.

In another embodiment, the DIS detector 404 and GEN detector 406 use data from the vertical displacement estimator 304, and/or the horizontal displacement estimator 306 to detect a dissipation activity and a generation activity. In another embodiment, the DW detector uses the data from the knee torque estimator 314 to identify a downward activity. In yet another embodiment, the UW detector 412 uses the data from the absolute thigh angle estimator 308 to identify an upward activity. The STS detector 414 can use the knee torque estimator 314 to identify an sit-to-stand activity, and the SIT detector 416 can use the absolute thigh angle estimator 308 to identify a sitting activity. It will be understood that the various detectors can use any number, or combination, of the estimators to identify the various activities.

The output of the detectors 402-416 is sent to an arbitration mechanism 418, which can evaluate the outputs of the detectors 402-416 to identify a current activity and determine an appropriate course of action. The arbitration mechanism 418 can make the determination at every foot-strike. In such an embodiment, an identified current activity may be valid for only one step time frame. Furthermore, activity transitions can made be independent of the proper detection of exit conditions. The arbitration mechanism 418 can take various forms, depending on the particular embodiment selected and the specific requirements of the POD 100. Examples of certain embodiments of the arbitration mechanism 418 include, but are not limited to, a state-machine, a heuristic model or rule-base, a fuzzy rule set, a rule-based transition table, a probabilistic inference engine, and the like.

As mentioned, the arbitration mechanism can identify different activities and determine if a transition from one activity to another is warranted. Thus, actions associated with the arbitration mechanism 418 can include, but are not limited to, switching to a new activity, adopting a fallback behavior to ensure user safety, maintaining the current activity or other suitable activities, and the like In addition, the detectors 402-416 can repeatedly detect different activities and modes without regards to the feasibility of the transition to the given activity to ensure robust activity detection. Accordingly, in certain embodiments, the arbitration mechanism 418 detects and evaluates both possible and non-possible transitions each time the activity definition module 206 is called. Thus, in certain embodiments, no a priori assumptions are made when evaluating the activity detectors 402-416, allowing for the testing of possible branching. The arbitration mechanism 418 can account for the quality and reliability of detector output, as well as enforce the various rules associated with feasible and allowed activity transitions, as discussed in greater detail below with reference to FIG. 5.

In certain embodiments, the arbitration mechanism 418 can take into account user safety when deciding whether to allow an inter-activity transition to occur. To ensure user safety, the arbitration mechanism 418 can override certain transitions even though it has determined that the transition is occurring with certainty if it deems the transition too dangerous. For example, assume that the INE estimates the relative vertical displacement between consecutive steps to be slightly below the minimum requirement to maintain the POD in stairs descent activity. Though this would normally cause the system to transition back to Fumbling Around mode, which can be quite dangerous to the user who may vault over a stiffened lower-limb POD 100, the arbitration mechanism can override the fumbling around transition with a forward progression transition, from which the downwards walking mode is accessible in case the user's activity so requires.

Following the inference results of the arbitration mechanism 418, a decision regarding current locomotion activity can be identified and provided to the parameters manager 420. The parameters manager 420 can retrieve a parameter set corresponding to the current locomotion activity from the parameters database 422. The parameters manager 420 can also provide the parameter set to the reactive layer 130 in order to update the reactive layer 130 with data regarding the new activity. For example, the parameter set can include position set points, controller gains, velocity set points, conditions for transitioning from one state to another, etc. The reactive layer 130 can use the parameter set to modify the POD's behavior accordingly. Additional details regarding the transitions between activities and modes will be described in greater detail below with reference to FIG. 5.

In some embodiments, the reactive layer's behavior can be modified whenever a new parameter set is passed to the reactive layer 130 from the parameters manager 420 of inference layer 120. For example, the reactive layer can have two states during one locomotion activity, such as a standing activity, and then transition to three or more states for a different locomotion activity, such as forward progression, downward, upward, etc., based on the parameter set received from the inference layer 120. The parameters manager 420 can also manage the transition between each locomotion activity so as to avoid disrupting device operation, since such disruptions can affect overall user safety.

In addition, the reactive layer control system 130 described in greater detail in U.S. Publication No. 2011/0125290 A1 and International Patent Application No. PCT/CA2008/000110, the disclosures of which are incorporated herein in its entirety, can further include a parameters manager similar to the parameters manager 420 of FIG. 4. The parameters manager 420 or the parameters manager of the reactive layer can be configured to ensure smooth system transitions from one parameter set to the next. Managing the parameters can reduce the jerkiness or unexpected device motions due to changes in the motion control system structure and/or gains. For example, when transitioning between locomotion activities showing significantly different knee behavior (e.g., transitioning from standing to stairs ascent), knee joint impedance can undergo significant changes, and the device may generate mechanical power to lift the user's mass over the POD shank section. The parameters manager 420 can monitor the transition to reduce the risk of the knee pushing the user back instead of properly lifting the user.

Certain embodiments of a parameters manager can use linear interpolation to change the critical reactive layer parameters from the previous values to the targeted new values.

Transition Management

As mentioned above, one role of the inference layer control system 120 is to identify a current locomotion activity of a POD's user and make appropriate updates. The activity definition module 206 can implement the inference processes that can distinguish between different activities and determine when to update the current system activity. While distinguishing between different activities and determining when to update the current system activity can be divided amongst the activity estimators 302-316 and arbitration mechanism 418, the detection of the specialized forward progression modes and/or fumbling around modes can be accomplished using the parallel activity detectors 402-416.

The embodiments described herein are directed towards the control of a POD 100 that can be used for locomotion activities commonly encountered during typical daily living activities. Accordingly the general activity detection strategy accounts for previously identified locomotion activities. More specifically, the embodiments described herein are able to detect activities associated with non-locomotor gait tasks, generative gait tasks, dissipative gait tasks, and forward progression gait tasks. In certain embodiments, the general activity detection scheme leading to the specific implementation of the parallel activity detectors can be summarized as follows, with reference to FIG. 5.

Figure 5:
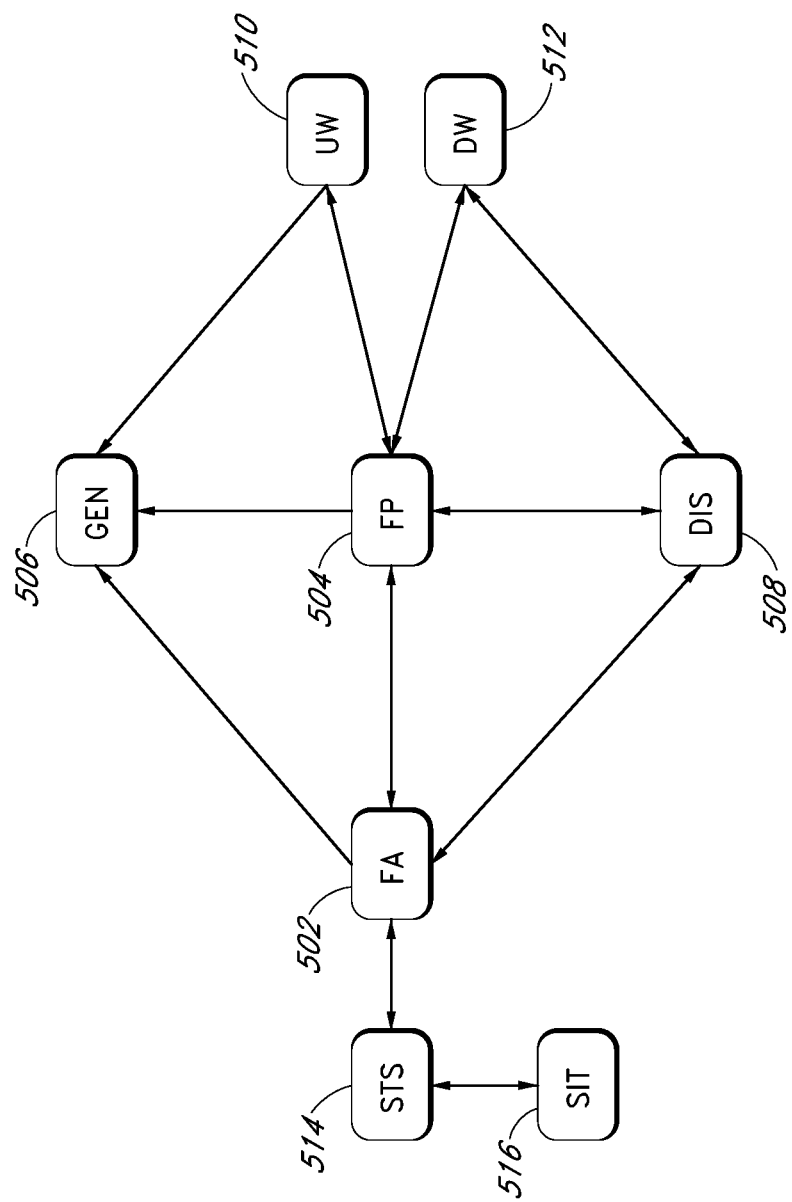
FIG. 5 is a state diagram depicting illustrative locomotion activities of an inference layer control system and transitions between the locomotion activities.

FIG. 5 is a block diagram illustrative of an embodiment of the different locomotion activities and modes and transitions between the activities, the FA modes and the FP modes. The various activities and modes include, but are not limited to, fumbling around (FA) 502, forward progression (FP) 504, generation (GEN) 506, dissipation (DIS) 508, upwards walking (UW) 510, downwards walking (DW) 512, sit-to-stand transfer (STS) 514 and sit (SIT) 516.

In an embodiment, the default state is the FA mode 502. Thus, unless more information is provided to the control system, the POD 100 operates under the general fumbling around low-level control strategy. While operating in the FA mode 502, the detection module can process data to detect activity transition to forward progression 504, generation 506, dissipation 508, or STS transfer 514, as illustrated in FIG. 5.

In an embodiment, the inference layer control system 120 transitions to, or detects, forward progression 504 when the user's center-of-mass moves the user's or a prosthetic limb's foot to within a certain threshold, coupled with detection of sufficient transition dynamics. The transition dynamics may include a predefined absolute thigh segment angle, a hip extension level (which may be measured using the thigh segment angle), an absolute thigh segment angle, and/or an acceleration of the thigh segment.

In an embodiment, the inference layer control system 120 transitions to, or detects, a generation 506 or dissipation 508 activity when the relative vertical displacement of the POD between consecutive foot strikes is larger than a pre-defined threshold. The relative vertical displacement of the POD can be based on the vertical displacement measured by a sensor, or a combination of sensors. For example, an average of the vertical displacement of multiple sensors can be used. This threshold can be based on the typical stair riser's height and the accuracy of the relative vertical displacement estimate. Alternatively, or in addition, the threshold can be based on the user's gait style, personal preferences, and/or the actual gait task being performed. For the generation activity 506, the relative vertical displacement may be greater than a pre-defined threshold, indicating an incline. For the dissipation activity 508, the relative vertical displacement may be less than a pre-defined threshold, indicating a decline.

In an embodiment, the inference layer control system 120 transitions to, or detects, upwards walking 510 or downwards walking 512 when the system is already operating in forward progression mode 504, generation mode 506, or dissipation mode 508. Detection of the downwards walking mode 512 can be triggered when the amplitude of the knee flexion torque is higher than a threshold value. The threshold value can be based on levels typically seen during the non-downwards walking forward progression mode. In this regard, the transition can be independent of the inertial navigation solution, which can provide an effective fallback mode that increases user safety even when the system is undergoing a temporary or permanent failure. Detection of the upwards walking mode 510 can be triggered when the amplitude of hip flexion during foot strikes rises above a pre-defined threshold. The amplitude of the hip flexion can be determined based on an absolute angle of the thigh segment. Detection of the upwards walking mode 510 and the downwards walking mode 512 can also be based on the ground slope, the vertical displacement of the POD, etc.

Transition to, or detection of, a sit-to-stand mode 514 can be triggered when the system is operating in fumbling around mode 502. The sit-to-stand mode 514 can be used to appropriately manage transitions between the fumbling around 502 and SIT mode 516. This can allow the system to manage dissipative or generative tasks associated with the lower-limbs when the user is sitting-down or standing-up. In an embodiment, dissipative sit-to-stand mode 514 is detected when the user is operating in the fumbling around mode 502 and the amplitude of the knee flexion torque rises above an adjustable threshold. A generative sit-to-stand mode 514 can be detected when sufficient hip extension dynamics are measured while the system is operating in the SIT mode 516. The detection of the SIT mode 516 or transfer to/from the dissipative sit-to-stand mode 514 can occur whenever the lower-limb POD 100 reaches a stable state, where the knee is flexed and the load is removed from the prosthetic device. For example, if the hip is flexed at or above ninety degrees when in swing phase the SIT mode 516 can be detected.

Systems and modules described herein may comprise, or may be embedded in a processing device, such as, software, firmware, hardware, or any combination(s) of software, firmware, or hardware suitable for the purposes described herein. In certain embodiments, software and other modules may reside on servers, workstations, personal computers, computerized tablets, PDAs, and/or an embedded computing device, such as embedded firmware (i.e., EPROM or EEPROM). In certain other embodiments, software and other modules may be accessible via local memory, a network, a browser, or other means suitable for the purposes described herein. In certain further embodiments, data structures or indexes described herein may comprise computer files, variables, programming arrays, programming structures, or any electronic information storage schemes or methods, or any combinations thereof, suitable for the purposes described herein.

Various embodiments are described herein with reference to flowchart illustrations and/or block diagrams of methods, apparatuses (systems), and computer program products. It will be understood that blocks of the flowchart illustrations and/or block diagrams, and combinations of blocks in the flowchart illustrations and/or block diagrams, may be implemented by computer program instructions. The blocks or states of the processes or methods described herein may be embodied directly in hardware, in a software module executed by a processor, embedded in firmware, or any combination thereof. In certain embodiments, the computer program instructions may be provided to a processor of a general purpose computer, special purpose computer, or other programmable data processing apparatus to produce a machine, such that the instructions, which execute via the processor of the computer or other programmable data processing apparatus, create means for implementing the acts specified in the flowchart and/or block diagram block or blocks. In certain embodiments, the processor may be located at least partially on, in, or remote to the POD 100 including the inference layer control system 120.

In certain other embodiments, these computer program instructions may be stored in a computer-readable memory, including computer-readable mediums integral to the processor, that can direct a computer or other programmable data processing apparatus to operate in a particular manner, such that the instructions stored in the computer-readable memory produce an article of manufacture including instruction means which implement the acts specified in the flowchart and/or block diagram block or blocks. In certain further embodiments, the computer program instructions may also be loaded onto a computer or other programmable data processing apparatus to cause a series of operations to be performed on the computer or other programmable apparatus to produce a computer implemented process such that the instructions which execute on the computer or other programmable apparatus provide means for implementing the acts specified in the flowchart and/or block diagram block or blocks. Moreover, readings from various measurement units and estimates from estimators can be downloaded or wirelessly transmitted to a remote computing device for further analysis of the user's gait.

Depending on the embodiment, certain acts, events, or functions of any of the processes or algorithms described herein can be performed in a different sequence, may be added, merged, or left out all together. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Conditional language used herein, such as, among others, "can," "could," "might," "may," "e.g.," "i.e.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements, and/or states are in any way required for one or more embodiments or that one or more embodiments necessarily include logic for deciding, with or without author input or prompting, whether these features, elements, and/or states are included or are to be performed in any particular embodiment.

Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z to each be present.

While the detailed description herein will show, describe, and point out various features as applied to various embodiments, it may be understood that various omissions, substitutions, and changes in the form and details of the logical blocks, modules, and processes illustrated may be made without departing from the spirit of the disclosure. As may be recognized, certain embodiments of the systems described herein may be embodied within a form that does not provide all of the features and benefits set forth herein, as some features may be used or practiced separately from others.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A control system for controlling a motorized prosthetic or orthotic device (POD) that is actuatable about a joint, the control system comprising:

a first inertial measurement unit (IMU) associated with a first segment of a POD and configured to collect a first set of data for determining one or more measurements of at least one of a vertical displacement of the first segment, a horizontal displacement of the first segment, a torque associated with the first segment, and an absolute angle of the first segment with respect to gravity;

a second IMU associated with a second segment of the POD and configured to collect a second set of data for determining one or more measurements of at least one of a vertical displacement of the second segment, a horizontal displacement of the second segment, a torque associated with the second segment, an absolute angle of the second segment with respect to gravity, and a net torque between the first segment and the second segment; and a control system architecture having an inference layer in communication with a reactive layer, wherein the inference and reactive layers are configured to each receive one or more first measurements and the one or more second measurements, and the reactive layer is further configured to control the POD based on one or more parameters of a motor controller, the inference layer comprising:

one or more locomotion activity detectors each configured to detect in parallel with each other a distinct locomotion activity of the user based on at least the one or more first measurements and the one or more second measurements;

an arbitration mechanism in communication with the one or more locomotion activity detectors and configured to evaluate outputs from the plurality of locomotion activity detectors to determine a current user activity;
and a parameters manager in communication with the arbitration mechanism, a parameters database and the reactive layer, the parameters manager configured to retrieve a parameter set from the parameters database based on the determined current user activity, and to provide the parameter set to the reactive layer to modify at least one parameter of the one or more parameters of the motor controller, wherein the at least one modified parameter alters a behavior of the reactive layer.

2. The control system of claim 1, wherein the POD comprises a shank segment coupled to an actuator by a compliant linkage.

3. The control system of claim 2, wherein the first segment is a segment in the actuator and the second segment is a segment in the shank segment.

4. The control system of claim 2, wherein the first segment is a segment in the actuator, and the second segment is a segment in the compliant linkage.

5. The control system of claim 2, wherein the second IMU is further configured to measure a deflection of the compliant linkage.

6. The control system of claim 1, wherein the inference layer is situated between the reactive layer and a learning layer.

7. The control system of claim 6, wherein the learning layer is configured to analyze system performance and changes to data and rule sets of the inference layer.

8. The control system of claim 1, wherein each locomotion activity detector of the one or more locomotion activity detectors of the inference layer is configured to identify at least one of fumbling around (FA), forward progression (FP), generation (GEN), dissipation (DIS), upward walking (UW), downward walking (DW), standing-to-sitting (STS), and sitting (SIT).

9. The control system of claim 1, wherein each IMU includes at least one of an accelerometer, a gyroscope, a kinematic sensor, and a torque sensor.

10. The control system of claim 1, wherein the inference layer further comprises at least one of a detection module, a performance assessment module and an activity definition module.

11. The control system of claim 1, wherein the inference layer further comprises a detection module comprising one or more estimators configured to estimate the one or more first measurements and the one or more second measurements based respectively on the first set of data and the second set of data.

12. A control system for controlling a motorized prosthetic or orthotic device (POD) that is actuatable about a joint, the control system comprising:
a first inertial measurement unit (IMU) associated with a first segment of a user and configured to collect a first set of data for determining one or more first measurements of at least one of a vertical displacement of the first segment, a horizontal displacement of the first segment, a torque associated with the first segment, and an absolute angle of the first segment with respect to gravity;
a second IMU associated with a second segment of the POD and configured to collect a second set of for determining one or more second measurements of at least one of a vertical displacement of the second segment, a horizontal displacement of the second segment, a torque associated with the second segment, an absolute angle of the second segment with respect to gravity, and a net torque between the first segment and the second segment; and
a control system architecture having an inference layer in communication with a reactive layer, wherein the inference and reactive layers are configured to each receive the one or more first measurements and the one or more second measurements, and the reactive layer is further configured to control the POD based on one or more parameters of a motor controller, the inference layer comprising:
a plurality of locomotion activity detectors each configured to detect in parallel with each other a distinct locomotion activity of the user based on at least the one or more first measurements and the one or more second measurements;
an arbitration mechanism in communication with the plurality of locomotion activity detectors and configured to evaluate outputs from the plurality of locomotion activity detectors to determine a current user activity;
and
a parameters manager in communication with the arbitration mechanism, a parameters database and the reactive layer, the parameters manager configured to retrieve a parameter set from the parameters database based on the determined current user activity, and to provide the parameter set to the reactive layer to modify at least one parameter of the one or more parameters of the motor controller, wherein the at least one modified parameter alters a behavior of the reactive layer.

13. The control system of claim 12, wherein the first segment is a thigh segment and the second segment is a shank segment.

14. The control system of claim 12, wherein the inference layer is situated between the reactive layer and a learning layer.

15. The control system of claim 14, wherein the learning layer is configured to analyze system performance and changes to data and rule sets of the inference layer.

16. The control system of claim 12, wherein each locomotion activity detector of the plurality of locomotion activity detectors of the inference layer is configured to identify at least one of fumbling around (FA), forward progression (FP), generation (GEN), dissipation (DIS), upward walking (UW), downward walking (DW), standing-to-sitting (STS), and sitting (SIT).

17. The control system of claim 12, wherein the inference layer further comprises at least one of a detection module, a performance assessment module and an activity definition module.

18. The control system of claim 12, wherein the first IMU is located at a distal portion of the first segment and the second IMU is located at a distal portion of the second segment.

19. The control system of claim 12, wherein each IMU includes at least one of an accelerometer, a gyroscope, a kinematic sensor, and a torque sensor.

20. The control system of claim 12, wherein the inference layer further comprises a detection module comprising one or more estimators configured to estimate the one or more first measurements and the one or more second measurements based respectively on the first set of data and the second set of data.

* * * * *

UNITED STATES PATENT AND TRADEMARK OFFICE
CERTIFICATE OF CORRECTION

| | | |
|---|---|---|
| PATENT NO. | : 9,925,071 B2 | Page 1 of 1 |
| APPLICATION NO. | : 14/549278 | |
| DATED | : March 27, 2018 | |
| INVENTOR(S) | : David Langlois et al. | |

It is certified that error appears in the above-identified patent and that said Letters Patent is hereby corrected as shown below:

In Column 1 (page 4, item (56)) at Line 53, Under Other Publications, change "prosthectics" to --prosthetics--.

In Column 1 (page 4, item (56)) at Line 56, Under Other Publications, change "request" to --requests--.

In Column 2 (page 4, item (56)) at Line 44, Under Other Publications, change "Tomovié" to --Tomović--.

In Column 17 at Line 55, Change "like" to --like.--.

In Column 23 at Line 51, In Claim 12, change "of" to --of data--.

Signed and Sealed this
Third Day of July, 2018

Andrei Iancu
*Director of the United States Patent and Trademark Office*